(12) United States Patent
Nixon et al.

(10) Patent No.: US 12,110,343 B2
(45) Date of Patent: Oct. 8, 2024

(54) ANTI-PLASMA KALLIKREIN ANTIBODIES

(71) Applicant: Takeda Pharmaceutical Company Limited, Osaka (JP)

(72) Inventors: Andrew Nixon, Hanover, MA (US); Jon A. Kenniston, Hingham, MA (US); Stephen R. Comeau, Avon, NY (US)

(73) Assignee: Takeda Pharmaceutical Company Limited, Osaka (JP)

( * ) Notice: Subject to any disclaimer, the term of this patent is extended or adjusted under 35 U.S.C. 154(b) by 400 days.

(21) Appl. No.: 17/684,460

(22) Filed: Mar. 2, 2022

(65) Prior Publication Data

US 2023/0002509 A1 Jan. 5, 2023

Related U.S. Application Data

(63) Continuation of application No. 16/199,453, filed on Nov. 26, 2018, now Pat. No. 11,299,553, which is a continuation of application No. 14/773,766, filed as application No. PCT/US2014/027100 on Mar. 14, 2014, now abandoned.

(60) Provisional application No. 61/791,822, filed on Mar. 15, 2013.

(51) Int. Cl.
    *C07K 16/40* (2006.01)

(52) U.S. Cl.
    CPC .......... *C07K 16/40* (2013.01); *C07K 2317/34* (2013.01); *C07K 2317/565* (2013.01); *C07K 2317/76* (2013.01); *C07K 2317/92* (2013.01)

(58) Field of Classification Search
    CPC ................................................ A61K 39/3955
    See application file for complete search history.

(56) References Cited

U.S. PATENT DOCUMENTS

| | | | |
|---|---|---|---|
| 5,045,452 A | 9/1991 | Spragg et al. | |
| 5,444,156 A | 8/1995 | Veloso et al. | |
| 5,880,256 A | 3/1999 | Dennis et al. | |
| 8,816,055 B2 | 8/2014 | Sexton et al. | |
| 8,822,653 B2 | 9/2014 | Sexton et al. | |
| 9,266,964 B2 | 2/2016 | Sexton et al. | |
| 10,316,095 B2 | 6/2019 | Fowler et al. | |
| 10,336,832 B2 | 7/2019 | Sexton et al. | |
| 10,370,453 B2 | 8/2019 | Sexton et al. | |
| 10,428,158 B2 | 10/2019 | Conley et al. | |
| 11,046,785 B2 | 6/2021 | Conley et al. | |
| 11,084,884 B2 | 8/2021 | Sexton et al. | |
| 11,286,307 B2 | 3/2022 | Adelman et al. | |
| 11,299,553 B2 | 4/2022 | Nixon et al. | |
| 11,401,346 B2 | 8/2022 | Sexton et al. | |
| 2003/0138417 A1 | 7/2003 | Kaisheva et al. | |
| 2003/0148271 A1 | 8/2003 | Hillman et al. | |
| 2007/0004910 A1 | 1/2007 | Sexton et al. | |
| 2007/0253949 A1 | 11/2007 | Golz et al. | |
| 2009/0105142 A1 | 4/2009 | Moscicki | |
| 2010/0285507 A1 | 11/2010 | Cho et al. | |
| 2011/0200611 A1 | 8/2011 | Sexton | |
| 2012/0201756 A1 | 8/2012 | Sexton | |
| 2012/0264798 A1 | 10/2012 | Sinha et al. | |
| 2013/0216556 A1 | 8/2013 | Fowler et al. | |
| 2014/0303357 A1 | 10/2014 | Lim et al. | |
| 2014/0335023 A1 | 11/2014 | Sexton et al. | |
| 2015/0274841 A1 | 10/2015 | Conley et al. | |
| 2015/0362492 A1 | 12/2015 | Joseph et al. | |
| 2016/0017055 A1 | 1/2016 | Nixon et al. | |
| 2016/0102150 A1 | 4/2016 | Sexton et al. | |
| 2017/0002094 A1 | 1/2017 | Sexton et al. | |
| 2018/0002447 A1 | 1/2018 | Sexton et al. | |
| 2018/0002448 A1 | 1/2018 | Sexton et al. | |
| 2018/0002449 A1 | 1/2018 | Sexton et al. | |
| 2018/0037664 A1 | 2/2018 | Sexton et al. | |
| 2018/0037665 A1 | 2/2018 | Sexton et al. | |
| 2018/0037666 A1 | 2/2018 | Sexton et al. | |
| 2018/0298110 A1 | 10/2018 | Chyung et al. | |
| 2018/0362664 A1 | 12/2018 | Adelman et al. | |
| 2019/0185580 A1 | 6/2019 | Nixon et al. | |
| 2020/0017602 A1 | 1/2020 | Sexton et al. | |
| 2020/0109213 A1 | 4/2020 | Sexton et al. | |
| 2020/0109214 A1 | 4/2020 | Peng et al. | |
| 2020/0115469 A1 | 4/2020 | Conley et al. | |
| 2020/0317815 A1 | 10/2020 | Mendivil Medina | |
| 2021/0087293 A1 | 3/2021 | Sexton et al. | |
| 2022/0033521 A1 | 2/2022 | Conley et al. | |
| 2022/0169749 A1 | 6/2022 | Chyung et al. | |

FOREIGN PATENT DOCUMENTS

| | | |
|---|---|---|
| BR | 112015017195 A2 | 7/2017 |
| BR | 112017020864 A2 | 7/2018 |
| CN | 1233256 A | 10/1999 |
| CN | 101928346 A | 12/2010 |

(Continued)

OTHER PUBLICATIONS

U.S. Appl. No. 17/842,999, filed Jun. 17, 2022, Sexton et al.
U.S. Appl. No. 17/672,748, filed Feb. 16, 2022, Adelman et al.
U.S. Appl. No. 17/745,770, filed May 16, 2022, Lu et al.
EP 14769643.9, Oct. 27, 2016, Extended European Search Report.
EP 19177968.5, Dec. 13, 2019, Extended European Search Report.
PCT/US2014/027100, Jun. 18, 2014, Invitation to Pay Additional Fees.

(Continued)

*Primary Examiner* — Prema M Mertz
(74) *Attorney, Agent, or Firm* — Wolf, Greenfield & Sacks, P.C.

(57) ABSTRACT

Disclosed herein are antibodies capable of binding to plasma kallikrein and inhibit its activity. Such antibodies interact with one or more critical residues in the catalytic domain of the plasma kallikrein. The antibodies may also contain specific heavy chain complementarity determining region 3 (CDRs) motifs and optionally specific residues at certain positions within both the heavy chain variable region and the light chain variable region.

10 Claims, 9 Drawing Sheets
Specification includes a Sequence Listing.

(56) References Cited

FOREIGN PATENT DOCUMENTS

| | | |
|---|---|---|
| CN | 103635489 A | 3/2014 |
| CN | 105051068 A | 11/2015 |
| EA | 2016/91470 A1 | 12/2016 |
| EA | 2017/92161 A1 | 4/2018 |
| JP | H9-509838 A | 10/1997 |
| JP | 2006-501168 A | 1/2006 |
| JP | 2008-514624 A | 5/2008 |
| JP | 2009-529553 A | 8/2009 |
| JP | 2013-516478 A | 5/2013 |
| JP | 2014-506257 A | 3/2014 |
| JP | 2014-515763 A | 7/2014 |
| JP | 6845012 B2 | 3/2021 |
| WO | WO 87/05396 A1 | 9/1987 |
| WO | WO 2004/018468 A2 | 3/2004 |
| WO | WO 2004/050658 A1 | 6/2004 |
| WO | WO 2005/085246 A1 | 9/2005 |
| WO | WO 2006/029769 A1 | 3/2006 |
| WO | WO 2006/036860 A2 | 4/2006 |
| WO | WO 2007/104541 A2 | 9/2007 |
| WO | WO 2011/085103 A3 | 7/2011 |
| WO | WO 2013/186700 A1 | 12/2013 |
| WO | WO 2014/113701 A1 | 7/2014 |
| WO | WO 2014/113712 A1 | 7/2014 |
| WO | WO 2014/152232 A2 | 9/2014 |
| WO | WO 2015/112578 A1 | 7/2015 |
| WO | WO 2016/160926 A1 | 10/2016 |
| WO | WO 2017/100679 A1 | 6/2017 |

OTHER PUBLICATIONS

PCT/US2014/027100, Sep. 10, 2014, International Search Report and Written Opinion.

PCT/US2014/027100, Sep. 24, 2015, International Preliminary Report on Patentability.

[No Author Listed] Dyax's DX-2930 granted Orphan Drug designation in hereditary angioedema. Dec. 6, 2013.

[No Author Listed] Efficacy and Safety Study of DX-2930 to prevent acute angioedema attacks in patients with Type I and Type II HAE. Study NCT02586805. ClinicalTrials.gov Apr. 9, 2019. 7pgs.

[No Author Listed] Fair Disclosure Wire, "Dyax Corp. announces positive results from phase 1a clinical trial of DX2930" dated Feb. 25, 2014. Last accessed from http://dialog.proquest.com/professional/printviewfile?accountid=157282 on May 20, 2016. p. 1-15.

[No Author Listed] Shire's Takhzyro expected to dominate in hereditary angioedema. Sep. 19, 2018;(1-3) https://clarivate.com/cortellis/blog/shires-takhzyro-anticipated-to-dominate-the-market-following-on-track-approval-in-hereditary-angioedema/ [last accessed on Feb. 27, 2020].

Almagro et al., Humanization of antibodies. Front Biosci. Jan. 1, 2008;13:1619-33. doi: 10.2741/2786.

Bagdasarian et al., Immunochemical studies of plasma kallikrein. J Clin Invest. Dec. 1974;54(6):1444-54.

Banerji et al., Effect of Lanadelumab Compared With Placebo on Prevention of Hereditary Angioedema Attacks: A Randomized Clinical Trial. JAMA. Nov. 27, 2018;320(20):2108-2121. doi: 10.1001/jama.2018.16773.

Banerji et al., Inhibiting Plasma Kallikrein for Hereditary Angioedema Prophylaxis. N Engl J Med. Feb. 23, 2017;376(8):717-728. doi: 10.1056/NEJMoa1605767.

Banerji et al., Lanadelumab 300mg every 2 weeks effectively prevented hereditary angioedema attacks in the help study. Ann Allerg Asthma Im. Nov. 1, 2018;121(5):S5.

Bendig, Humanization of Rodent Monoclonal Antibodies by CDR Grafting. Companion to Methods in Enzymology. 1995;8:83-93.

Bova et al., Lanadelumab Injection Treatment for the Prevention of Hereditary Angioedema (HAE): Design, Development and Place in Therapy. Drug Des Devel Ther. Oct. 22, 2019;13:3635-3646. doi: 10.2147/DDDT.S192475.

Breedveld, Therapeutic monoclonal antibodies. Lancet. Feb. 26, 2000;355(9205):735-40. Review.

Busse et al., Efficacy and safety of lanadelumab for prophylactic treatment in adolescents with hereditary angioedema (HAE). Feb. 2019;143(2):AB43.

Busse et al., Lanadelumab for the Prophylactic Treatment of Hereditary Angioedema with C1 Inhibitor Deficiency: A Review of Preclinical and Phase I Studies. BioDrugs. Feb. 2019;33(1):33-43. doi: 10.1007/s40259-018-0325-y.

Carrol, Shire wins a blockbuster OK for pipeline star lanadelumab, boosting Takeda's $62B takeover deal. Endpoint News. Aug. 23, 2018;(1-5) https://endpts.com/shire-wins-a-blockbuster-ok-for-pipeline-star-lanadelumab-boosting-takedas-62b-takeover-deal/ [last accessed Feb. 27, 2020].

Casset et al., A peptide mimetic of an anti-CD4 monoclonal antibody by rational design. Biochem Biophys Res Commun. Jul. 18, 2003;307(1):198-205.

Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.

Faucette et al., Biomarker Assay for the detection of contact system activation. Ameri Soc. Hemato. Nov. 15, 2013; 122(21):2347. 55th Annual Meeting of the American Society-of-Hematology. New Orleans, LA, USA. Dec. 7-10, 2013.

Feener, Plasma kallikrein and diabetic macular edema. Curr Diab Rep. Aug. 2010;10(4):270-5. doi: 10.1007/s11892-010-0127-1.

Ferrara et al., Recombinant renewable polyclonal antibodies. MAbs. 2015;7(1):32-41. doi: 10.4161/19420862.2015.989047.

Fink et al., Cellular expression of plasma prekallikrein in human tissues. Biol Chem. Sep. 2007;388(9):957-63.

Frank, 8. Hereditary angioedema. J Allergy Clin Immunol. Feb. 2008;121(2 Suppl):S398-401; quiz S419. doi: 10.1016/j.jaci.2007.07.057.

Frank et al., Management of Children With Hereditary Angioedema Due to C1 Inhibitor Deficiency. Pediatrics. Nov. 2016;138(5):e20160575. doi: 10.1542/peds.2016-0575.

Gao et al., Extracellular carbonic anhydrase mediates hemorrhagic retinal and cerebral vascular permeability through prekallikrein activation. Nat Med. Feb. 2007;13(2):181-8. Epub Jan. 28, 2007.

Green, Antibody engineering via genetic engineering of the mouse: XenoMouse strains are a vehicle for the facile generation of therapeutic human monoclonal antibodies. J Immunol Methods. Dec. 10, 1999;231(1-2):11-23.

Holliger et al., Engineered antibody fragments and the rise of single domains. Nat Biotechnol. Sep. 2005;23(9):1126-36.

Janeway et al., The interaction of the antibody molecule with specific antigen. Immunobiology: The Immune System in Health and Disease.5th edition. New York: Garland Science; 2001. NCBI Bookshelf. 5 pages.

Kenniston et al., Discovery and Characterization of a Highly Specific Antibody Inhibitor of Plasma Kallikrein. Blood 2013;122:1067. Abstract only.

Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.

Kettleborough et al., Humanization of a mouse monoclonal antibody by CDR-grafting: the importance of framework residues on loop conformation. Protein Eng. Oct. 1991;4(7):773-83.

Lederman et al., A Single Amino Acid Substitution in a Common African Allele of the CD4 Molecule Ablates Binding of the Monoclonal Antibody, OKT4. Molecular Immunology. 1991;28(11):1171-1181.

Levy et al., The therapeutic potential of a kallikrein inhibitor for treating hereditary angioedema. Expert Opin Investig Drugs. Sep. 2006;15(9):1077-90.

Li et al., β-Endorphin omission analogs: Dissociation of immunoreactivity from other biological activities. Proc. Natl. Acad. Sci. USA. Jun. 1980;77(6):3211-3214.

Liu et al., Plasma kallikrein-kinin system and diabetic retinopathy. Biol Chem. Mar. 2013;394(3):319-28. doi: 10.1515/hsz-2012-0316. Author manuscript.

Lloyd et al., Modelling the human immune response: performance of a 1011 human antibody repertoire against a broad panel of

(56) References Cited

OTHER PUBLICATIONS therapeutically relevant antigens. Protein Eng Des Sel. Mar. 2009;22(3):159-68. doi: 10.1093/protein/gzn058. Epub Oct. 29, 2008.

Lumry et al., Subcutaneous self-administration of lanadelumab for prophylactic treatment in patients with hereditary angioedema (HAE). Ann Allerg Asthma Im. Nov. 2018;121(5):S57.

MacCallum et al., Antibody-antigen interactions: contact analysis and binding site topography. J Mol Biol. Oct. 11, 1996;262(5):732-45.

Okano et al., Chapter 9.1.2 Drug Action and Blood Concentration. Shin Yakuzaiaku Soron, revised 3rd Edition, Apr. 10, 1987:250-253.

Ornskov et al., Shire Reports Positive Topline Phase 3 Results for Lanadelumab (SHP643) in Patients With Hereditary Angioedema (HAE). Shire Investor Presentation. May 18, 2017. Presentation. 10 pgs.

Paul. Fv Structure and Diversity in Three Dimensions. Fundamental Immunology, 3rd Edition. 1993: 292-5.

Phipps et al., Plasma kallikrein mediates angiotensin II type 1 receptor-stimulated retinal vascular permeability. Hypertension. Feb. 2009;53(2):175-81. doi:10.1161/HYPERTENSIONAHA.108.117663. Epub Jan. 5, 2009. With 5 page Online Supplement.

Riedl et al., An open-label study to evaluate the long-term safety and efficacy of lanadelumab for prevention of attacks in hereditary angioedema: design of the HELP study extension. Clin Transl Allergy. Oct. 6, 2017;7:36. doi: 10.1186/s13601-017-0172-9.

Schneider et al., Critical role of kallikrein in hereditary angioedema pathogenesis: a clinical trial of ecallantide, a novel kallikrein inhibitor. J Allergy Clin Immunol. Aug. 2007;120(2):416-22. Epub Jun. 7, 2007.

Sela-Culang et al., The structural basis of antibody-antigen recognition. Front Immunol. Oct. 8, 2013;4:302. doi: 10.3389/fimmu.2013.00302.

Sexton et al., Comparison of Plasma Kallikrein Inhibition by the Endogenous C1-Inhibitor Versus DX-2930, a Monoclonal Antibody Inhibitor. Blood. 2013;122:1066. Abstract only.

Sexton et al., Discovery and characterization of fully human monoclonal antibody inhibitor of plasma kallikrein for the treatment of plasma kallikrein-mediated edema. J Allergy Clin Immunol. Feb. 2013;131(2):AB32. Suppl S. Annual meeting of the American Academy of Allergy, Asthma, and Immunology. San Antonio, TX, USA; Feb. 22-26.

Sexton et al., Specific inhibition of tissue kallikrein 1 with a human monoclonal antibody reveals a potential role in airway diseases. Biochem J. Aug. 13, 2009;422(2):383-92. doi: 10.1042/BJ20090010.

Shariat-Madar et al., Assembly and activation of the plasma kallikrein/kinin system: a new interpretation. Int Immunopharmacol. Dec. 2002;2(13-14):1841-9.

Tang et al., Expression, crystallization, and three-dimensional structure of the catalytic domain of human plasma kallikrein. J Biol Chem. Dec. 9, 2005;280(49):41077-89. Epub Sep. 30, 2005.

Varghese, Shire's drug for rare swelling disorder wins European panel green light. Physician's Weekly. Oct. 19, 2018;(1-3) https://www.reuters.com/article/us-shire-ema-takhzyro/shires-drug-for-rare-swelling-disorder-wins-european-panel-green-light-idUSKCN1MT1SQ [last accessed Feb. 27, 2020].

Veloso et al., A monoclonal anti-human plasma prekallikrein antibody that inhibits activation of prekallikrein by factor XIIa on a surface. Blood. Oct. 1987;70(4):1053-62.

Veronez et al., The involvement of proteoglycans in the human plasma prekallikrein interaction with the cell surface. PLoS One. Mar. 12, 2014;9(3):e91280. doi: 10.1371/journal.pone.0091280. eCollection 2014.

Walpole et al., The weight of nations: an estimation of adult human biomass. BMC Public Health. Jun. 18, 2012;12:439. doi: 10.1186/1471-2458-12-439.

Wang et al., Antibody structure, instability, and formulation. J Pharm Sci. Jan. 2007;96(1):1-26. doi: 10.1002/jps.20727.

Weaver, Animal studies paint misleading picture. Nature International Weekly Journal of Science. Published online Mar. 30, 2010. Retrieved on Aug. 1, 2017 from http://www.nature.com/news.2010.158.html.

Wedi, Lanadelumab to treat hereditary angioedema. Drugs Today (Barc). Jul. 2019;55(7):439-448. doi: 10.1358/dot.2019.55.7.2985293.

Wedner et al., Modeling and Analyses to Identify Potential Dosing Regimens of DX-2930 for the Long-Term Prophylaxis of Hereditary Angioedema. J All Clin Immunol. Feb. 1, 2016;137(2):AB252.

Wu, Lanadelumab for the treatment of hereditary angioedema. Expert Opin Biol Ther. Dec. 2019; 19(12):1233-1245. doi: 10.1080/14712598.2019.1685490. Epub Nov. 4, 2019.

Zuraw, Hae therapies: past present and future. Allergy Asthma Clin Immunol. Jul. 28, 2010;6(1):23. doi: 10.1186/1710-1492-6-23.

Figure 1

Light V gene = VK1_L12 HK102/V1/L12a;  J gene = JK1

```
                    FR1                          CDR1              FR2              CDR2
559A-M0162-A04: DIQMTQSPSTLSASVGDRVTITC RASQSISSWLA WYQQKPGKAPNLLIY KASTLES
                DIQMTQSPSTLSASVGDRVTITC RASQSISSWLA WYQQKPGKAP LLIY AS+LES
Germline:       DIQMTQSPSTLSASVGDRVTITC RASQSISSWLA WYQQKPGKAPKLLIY DASSLES FR3                          CDR3           FR4
559A-M0162-A04: GVPSRFSGSGSGTEFTLTISSLQPDDFATYC QQYNTYWT FGQGTKVEIK (SEQ ID NO: 34)
                GVPSRFSGSGSGTEFTLTISSLQPDDFATYC QQYN+YWT FGQGTKVEIK (SEQ ID NO: 35)
Germline:       GVPSRFSGSGSGTEFTLTISSLQPDDFATYC QQYNSYWT FGQGTKVEIK (SEQ ID NO: 36)
```

Heavy V gene = VH3_3-23;  J gene = JH3

```
                    FR1                              CDR1     FR2              CDR2
559A-M0162-A04: EVQLLESGGGLVQPGGSLRLSCAASGFTFS HYIMM WVRQAPGKGLEWVS GIYSSGGITVYADSVKG
                EVQLLESGGGLVQPGGSLRLSCAASGFTFS Y M   WVRQAPGKGLEWVS I  SGG T YADSVKG
Germline:       EVQLLESGGGLVQPGGSLRLSCAASGFTFS SYAMS WVRQAPGKGLEWVS AISGSGGSTYYADSVKG FR3                                    CDR3            FR4
559A-M0162-A04: RFTISRDNSKNTLYLQMNSLRAEDTAVYYCAY RRTGIPRRDAFDI WGQGTMVTVSS (SEQ ID NO:37)
                RFTISRDNSKNTLYLQMNSLRAEDTAVYYCA             AFDI WGQGTMVTVSS (SEQ ID NO:38)
Germline:       RFTISRDNSKNTLYLQMNSLRAEDTAVYYCAK            AFDI WGQGTMVTVSS (SEQ ID NO:39)
```

Figure 2

```
391
     IVGGTNSSWG EWPWQVSLQV KLTAQRHLCG GSLIGHQWVL TAAHCFDGLP    440

441
     LQDVWRIYSG ILNLSDITKD TPFSQIKEII IHQNYKVSEG NHDIALIKLQ    490

491
     APLNYTEFQK PISLPSKGDT STIYTNCWVT GWGFSKEKGE IQNILQKVNI    540

541
     PLVTNEECQK RYQDYKITQR MVCAGYKEGG KDACKGDSGG PLVCKHNGMW    590

591
     RLVGITSWGE GCARREQPGV YTKVAEYMDW ILEKTQSSDG KAQMQSPA      638

(SEQ ID NO: 40)
```

Figure 3 (Cont'd)
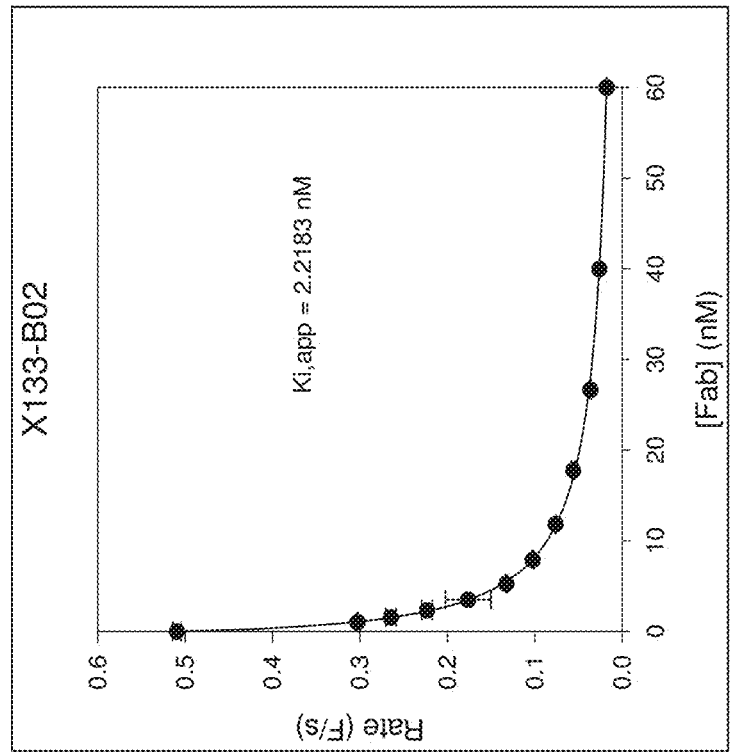
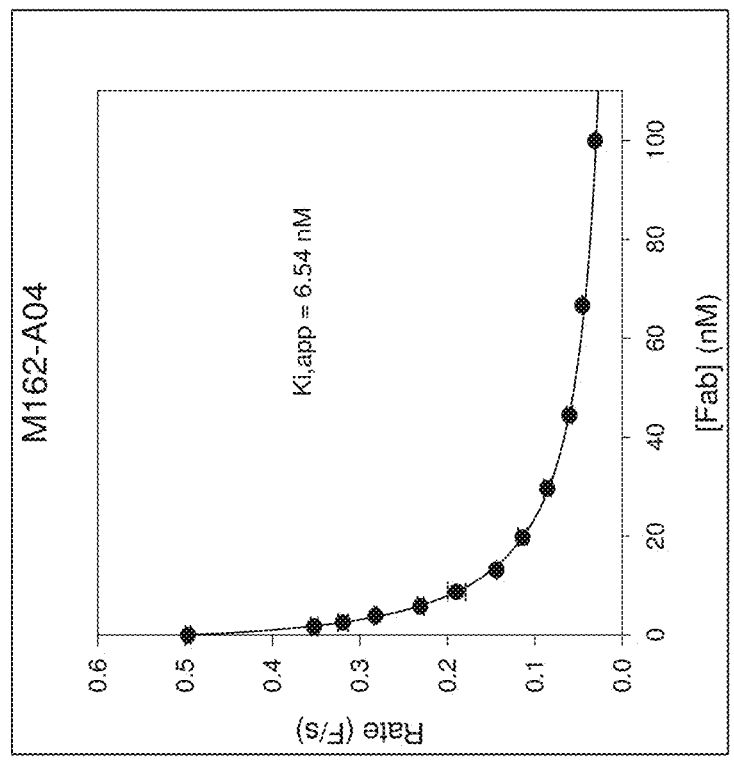

Figure 5

```
                            391                                                                        440
(klkb1)-Mut1-forPichia      IVGGTNSSWG  EWPWQVSLQV  KLTAQRHLCG  GSLIGHQWVL  TAAHCFDGLP
(klkb1)-Mut2-forPichia      IVGGTNSSWG  EWPWQVSLQV  KLTAQRHLCG  GSLIGHQWVL  TAAHCFDGLP
(klkb1)-Mut3-forPichia      IVGGTNSSWG  EWPWQVSLQV  KLTAQRHLCG  GSLIGHQWVL  TAAHCFDGLP
(klkb1)-Mut4-forPichia      IVGGTASAAG  EWPWQVSLQV  KLTAQRHLCG  GSLIGHQWVL  TAAHCFDGLP
(klkb1)-parentforPichia     IVGGTNSSWG  EWPWQVSLQV  KLTAQRHLCG  GSLIGHQWVL  TAAHCFDGLP 441                                                                        490
(klkb1)-Mut1-forPichia      LQDVWRIYSG  ILNLSDITKD  TPFSQIKEII  IHQNYKVAEG  AHDIALIKLQ
(klkb1)-Mut2-forPichia      LQDVWRIYSG  ILNLSDITKD  TPFSQIKEII  IHQNYKVSEG  NHDIALIKLQ
(klkb1)-Mut3-forPichia      LQDVWRIYSG  ILNLSDITKD  TPFSQIKEII  IHQNYKVSEG  NHDIALIKLQ
(klkb1)-Mut4-forPichia      LQDVWRIYSG  ILNLSDITKD  TPFSQIKEII  IHQNYKVSEG  NHDIALIKLQ
(klkb1)-parentforPichia     LQDVWRIYSG  ILNLSDITKD  TPFSQIKEII  IHQNYKVSEG  NHDIALIKLQ 491                                                                        540
(klkb1)-Mut1-forPichia      APLNYTEFQK  PISLPAAGDT  STIYTNCWVT  GWGFSKEKGE  IQNILQKVNI
(klkb1)-Mut2-forPichia      APLNYTEFQK  PISLPSKGDT  STIYTNCWVT  GWGFSKEKGE  IQNILQKVNI
(klkb1)-Mut3-forPichia      APLNYTEFQK  PISLPSKGDT  STIYTNCWVT  GWGFSKEKGE  IQNILQKVNI
(klkb1)-Mut4-forPichia      APLNYTEFQK  PISLPSKGDT  STIYTNCWVT  GWGFSKEKGE  IQNILQKVNI
(klkb1)-parentforPichia     APLNYTEFQK  PISLPSKGDT  STIYTNCWVT  GWGFSKEKGE  IQNILQKVNI 541                                                                        590
(klkb1)-Mut1-forPichia      PLVTNEECQK  RYQDYKITQR  MVCAGYKEGG  KDACKGDSGG  PLVCKHNGMW
(klkb1)-Mut2-forPichia      PLVTNEECQK  AYADAKIAQA  MVCAGYKEGG  KDACKGDSGG  PLVCKHNGMW
(klkb1)-Mut3-forPichia      PLVTNEECQK  RYQDYKITQR  MVCAGYKEGG  KAACAGASGG  PLVCKHNGMW
(klkb1)-Mut4-forPichia      PLVTNEECQK  RYQDYKITQR  MVCAGYKEGG  KDACKGDSGG  PLVCKHNGMW
(klkb1)-parentforPichia     PLVTNEECQK  RYQDYKITQR  MVCAGYKEGG  KDACKGDSGG  PLVCKHNGMW
```

Figure 5 (Cont'd)

```
                591                                                                              638
                 |                                                                                |
(klkb1)-Mut1-forPichia    RLVGITSWGE  GCARREQPGV  YTKVAEYMDW  ILEKTQSSDG  KAQMQSPA(SEQ ID NO: 41)
(klkb1)-Mut2-forPichia    RLVGITSWGE  GCARREQPGV  YTKVAEYMDW  ILEKTQSSDG  KAQMQSPA(SEQ ID NO: 42)
(klkb1)-Mut3-forPichia    RLVGITSWGE  GCARREQPGV  YTKVAEYMDW  ILEKTQSSDG  KAQMQSPA(SEQ ID NO: 43)
(klkb1)-Mut4-forPichia    RLVGITSWGE  GCARREQPGV  YTKVAEYMDW  ILEKTQSSDG  KAQMQSPA(SEQ ID NO: 44)
(klkb1)-parentforPichia   RLVGITSWGE  GCARREQPGV  YTKVAEYMDW  ILEKTQSSDG  KAQMQSPA(SEQ ID NO: 45)
```

ANTI-PLASMA KALLIKREIN ANTIBODIES

CROSS-REFERENCE TO RELATED APPLICATIONS

This application is a continuation of U.S. application Ser. No. 16/199,453, filed Nov. 26, 2018, which is a continuation of U.S. application Ser. No. 14/773,766, filed Sep. 9, 2015, which is a national stage filing under 35 U.S.C. § 371 of international PCT application PCT/US2014/027100, filed Mar. 14, 2014, which claims the benefit of U.S. Provisional Application No. 61/791,822, filed Mar. 15, 2013, each of which is incorporated by reference herein in its entirety.

SEQUENCE LISTING

The instant application contains a Sequence Listing which has been submitted electronically in ASCII format and is hereby incorporated by reference herein in its entirety. Said ASCII copy, created on Feb. 29, 2024, is named D061770033US03-SUBSEQ-EMB.txt and is 37,119 bytes in size.

BACKGROUND OF THE INVENTION

Plasma kallikrein is a serine protease component of the contact system and a potential drug target for different inflammatory, cardiovascular, infectious (sepsis) and oncology diseases (Sainz I. M. et al., Thromb Haemost 98, 77-83, 2007). The contact system is activated by either factor XIIa upon exposure to foreign or negatively charged surfaces or on endothelial cell surfaces by prolylcarboxypeptidases (Sainz I. M. et al., Thromb Haemost 98, 77-83, 2007). Activation of the plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature. A genetic deficiency in the C1-inhibitor protein (C1-INH), the major natural inhibitor of plasma kallikrein, leads to hereditary angioedema (HAE). Patients with HAE suffer from acute attacks of painful edema often precipitated by unknown triggers (Zuraw B. L. et al., N Engl J Med 359, 1027-1036, 2008).

Through the use of pharmacological agents or genetic studies in animal models, the plasma kallikrein-kinin system (plasma KKS) has been implicated in various diseases. Thus, it is of great interest to identify agents that inhibit plasma kallikrein activity, thereby effective in treating diseases associated with plasma kallikrein.

SUMMARY OF THE INVENTION

The present invention is based on the determination of crystal structures of a complex formed by the catalytic domain of human plasma kallikrein (PKal) and the Fab fragment of DX2930 (an antibody specifically binds human PKal and effectively inhibits its activity), and the identification of residues in both plasma kallirein (PKal) and the antibody that are critical to the interaction between the two molecules and/or to the inhibition of the pKal activity.

Accordingly, the present disclosure features anti-PKal antibodies capable of inhibiting its activity (e.g., by at least 50%), pharmaceutical compositions comprising such, and uses of the pharmaceutical compositions for treating diseases and disorders associated with plasma kallikrein.

In one aspect, the present disclosure provides an isolated antibody that binds human plasma kallikrein (PKal), wherein the antibody interacts with one or more of amino acid residues in the human PKal and inhibits its activity by at least 50%. The amino acid residues in the PKal that interact with the antibody can be V410, L412, T413, A414, Q415, R416, L418, C419, H434, C435, F436, D437, G438, L439, W445, Y475, K476, V477, S478, E479, G480, D483, F524, E527, K528, Y552, D554, Y555, A564, D572, A573, C574, K575, G576, S578, T596, S597, W598, G599, E600, G601, C602, A603, R604, Q607, P608, G609, V610, and Y611 as indicated in FIG. 2 (boldfaced and underlined).

In some examples, the anti-PKal antibody can bind an epitope of the PKal, the epitope comprising one of the following segments in PKal (FIG. 2): V410-C419, H434-L439, Y475-G480, F524-K528, Y552-Y555, D572-S578, T596-R604, or Q607-Y611.

In other examples, the antibody preferentially binds the PKal as relative to a mutant of the PKal (e.g., an inactive mutant) that contains one or more mutations at positions R551, Q553, Y555, T558, and R560 (e.g., Mutant 2 shown in FIG. 5).

In another aspect, the present disclosure provides an isolated antibody that binds human plasma kallikrein, wherein the antibody comprises a heavy chain variable region that comprises complementarity determining region 1 (HC CDR1), complementarity determining region 2 (HC CDR2), and complementarity determining region 3 (HC CDR3). The HC CDR3 in the antibody comprises the motif $X_{99}R_{100}X_{101}G_{102}X_{103}P_{104}R_{105}X_{106}X_{107}X_{108}X_{109}X_{110}X_{111}$ (SEQ ID NO: 58), in which $X_{99}$ is R or Q, $X_{101}$ is T, I, R, S, or P, $X_{103}$ is V, I, or L, $X_{106}$ is R or W, $X_{107}$ is D or N, $X_{108}$ is A, S, D, E, or V, $X_{109}$ is F or L, $X_{110}$ is D, E, or N, and Xiii is I, N, M, or S.

In some examples, $X_{99}$ can be Q and $X_{101}$ can be I, R, S, or P. In other examples, $X_{106}$ can be W and $X_{111}$ can be N, M, or S. Alternatively or in addition, $X_{101}$ can be I, $X_{108}$ can be E, and $X_{103}$ can be I or L. In yet other examples, $X_{101}$ can be I and $X_{103}$ can be I or L, or $X_{103}$ can be I or L and $X_{110}$ can be D, E, or N.

In some embodiments, the heavy chain variable region of the anti-PKal antibody described herein includes $H_{31}$ in the HC CDR1. Alternatively or in addition, the heavy chain variable region includes $F_{27}$, $F_{29}$, or both in the framework region 1 (FR1).

The anti-PKal antibody described herein can further comprise a light chain variable region that comprises complementarity determining region 1 (LC CDR1), complementarity determining region 2 (LC CDR2), and complementarity determining region 3 (LC CDR3). In some embodiments, the LC CDR2 includes $K_{50}$, $L_{54}$, $E_{55}$, $S_{56}$, or a combination thereof. Alternatively or in addition, the light chain variable region further includes $G_{57}$ in the framework region 3 (FR3). When necessary, the light chain variable includes $N_{45}$ in the framework region 2 (FR2).

Any of the anti-PKal antibodies described herein can inhibit the activity of PKal by at least 50% (e.g., at least 80%, 90%, 95%, or 99%). In some instances, the antibody has an apparent Ki ($K_{i,app}$) lower than about 1 nM (e.g., lower than about 0.1 nM, or lower than about 0.05 nM). Alternatively or in addition, the anti-PKal antibody described herein can have a binding affinity ($K_D$) for the PKal of less than $10^{-6}$ M (e.g., less than $10^{-7}$ M, $10^{-8}$ M, or $10^{-9}$ M).

The anti-PKal antibodies described herein can be a full-length antibody or an antigen-binding fragment thereof.

Alternatively or in addition, the antibody can be a human antibody or a humanized antibody.

Also within the scope of the present disclosure are pharmaceutical compositions for use in treating various diseases and disorders associated with plasma kallikrein, or for use in manufacturing a medicament for treating the diseases and disorders. The pharmaceutical compositions each comprise one or more anti-PKal antibodies as described herein and a pharmaceutically acceptable carrier.

Further, described herein are methods for treating a disease associated with plasma kallikrein, comprising administering to a subject in need thereof an effective amount of the pharmaceutical composition, which comprises one or more of the anti-PKal antibodies described herein. In some examples, the subject is a human patient diagnosed with, suspected of having, or at risk for the disease.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 1 shows the amino acid sequence of the heavy chain variable region ($V_H$) and light chain variable region ($V_L$) of a parent antibody, M0162-A04, from which DX2930 was derived, and their alignment with the corresponding germline $V_H$ and $V_L$ genes as indicated. The M0162-A04 $V_L$ complementarity determining region (CDR) 1 corresponds to SEQ ID NO: 59, $V_L$ CDR2 corresponds to SEQ ID NO: 60, $V_L$ CDR3 corresponds to SEQ ID NO: 61, $V_H$ CDR1 corresponds to SEQ ID NO: 62. $V_H$ CDR2 corresponds to SEQ ID NO: 63, and $V_H$ corresponds to SEQ ID NO: 64. Variations in M0162-A04 as compared to the germline sequences are indicated (boldfaced).

FIG. 2 shows the amino acid sequence (SEQ ID NO:40) of the catalytic domain of human plasma kallikrein (residues 391-638 of the full length human PKal). The boldfaced and underlined residues refer to those that are involved in the interaction with the Fab fragment of DX2930 as identified by the crystal structure discussed in Example 1 below.

FIG. 5 shows the amino acid sequences of a number of PKal mutants (catalytic domain), which were produced in *Pichia* cells.

DETAILED DESCRIPTION OF THE INVENTION

Figure 3:
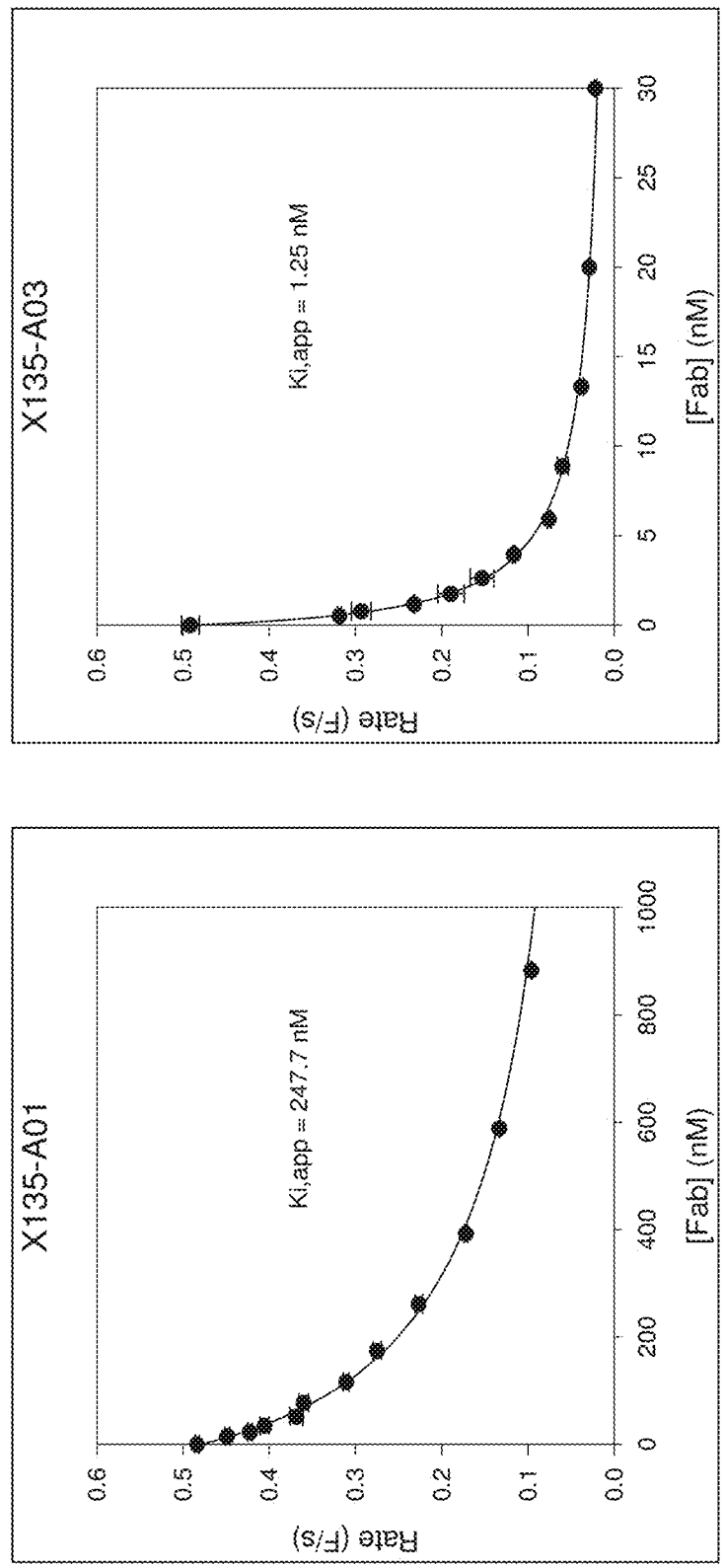
FIG. 3 is a graph showing the apparent Ki ($K_{i, app}$) of a number of antibody mutants derived from M0162-A04 against human PKal.
Figure 3:
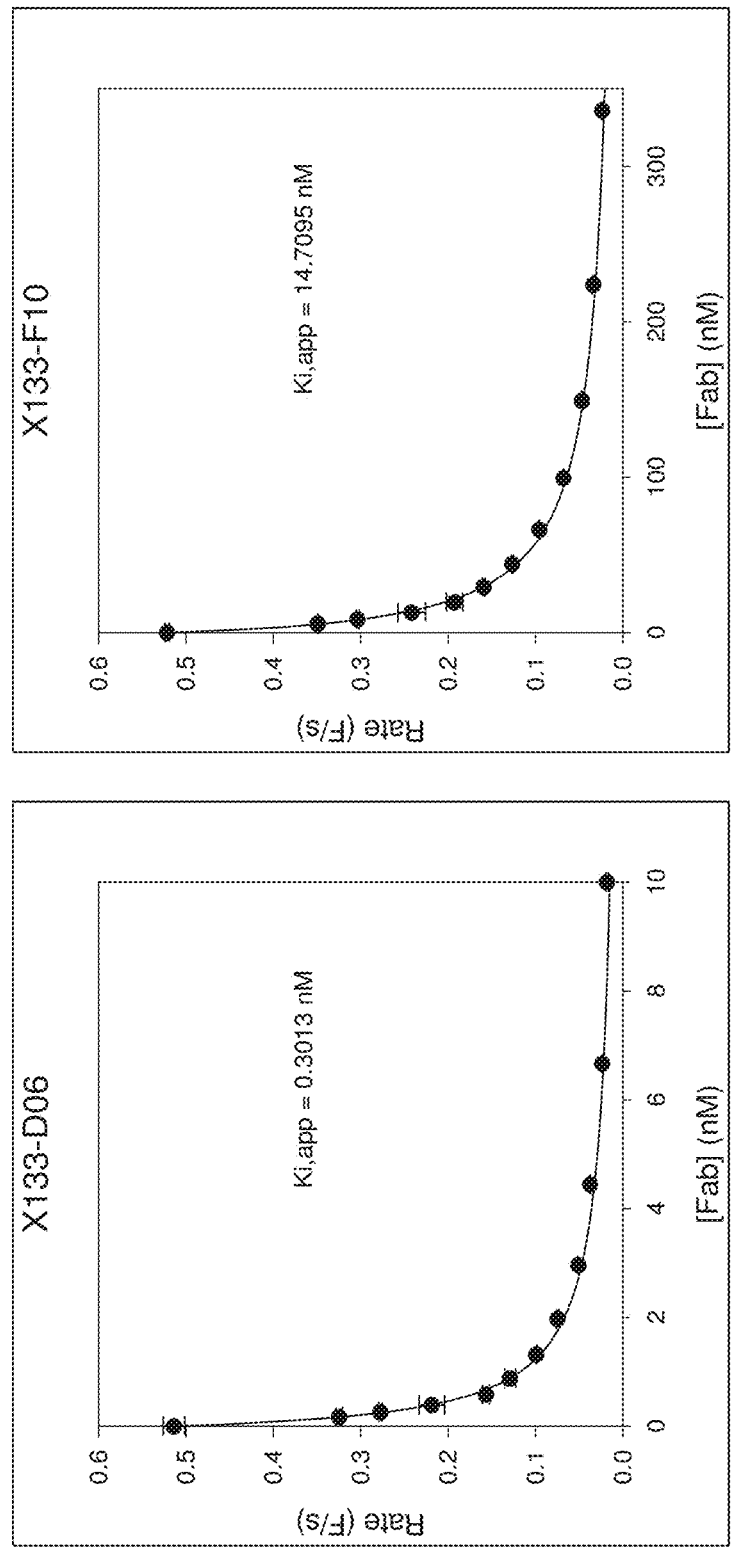
Figure 3:
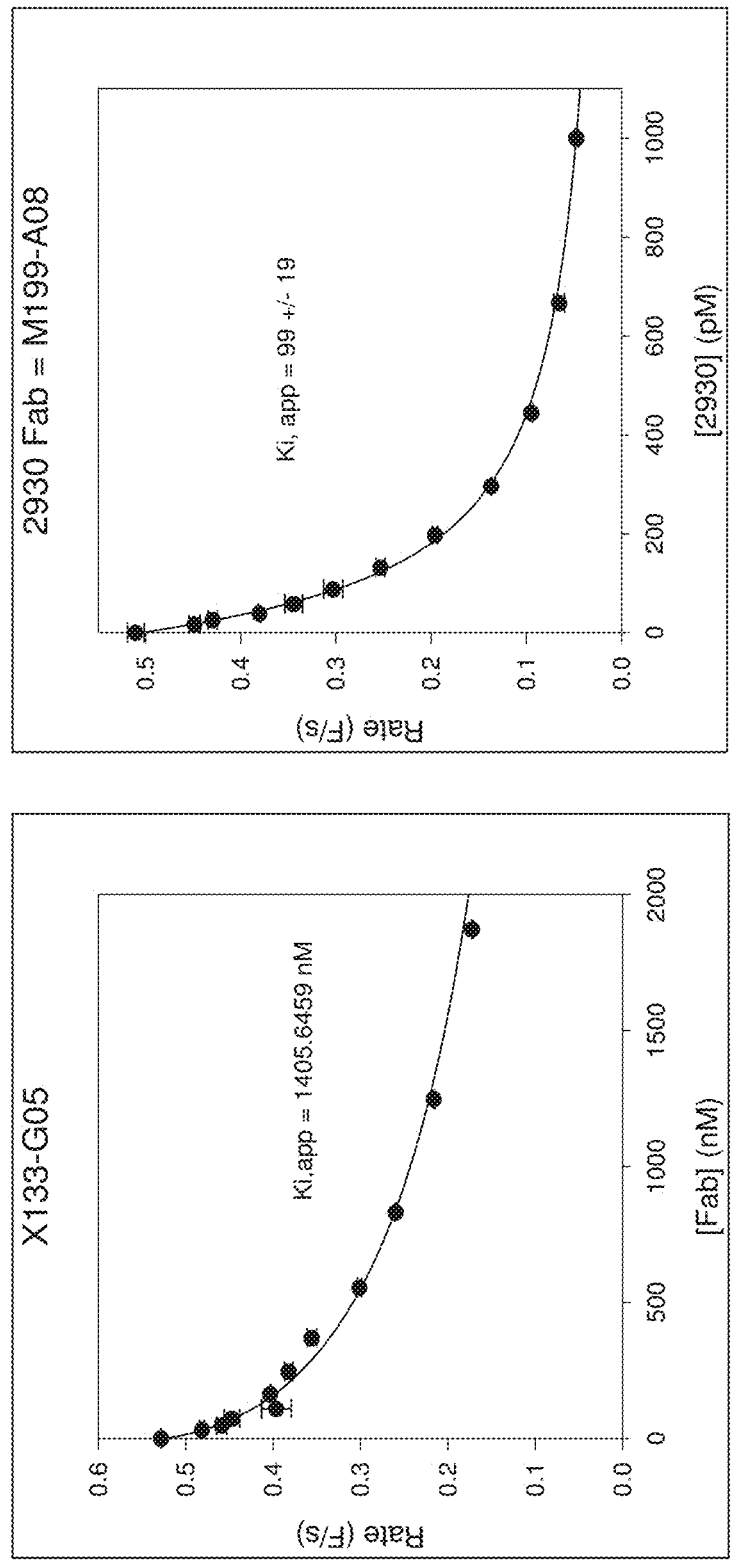

DX-2930 is a fully human IgG derived from parent clone M0162-A04. The amino acid sequences of the $V_H$ and $V_L$ of M0162-A04 are shown in FIG. 1. Their alignment with the corresponding germline VH gene (VH3_3-23) and VL gene (VK1_L12) is also shown in FIG. 1. Compared to the HC CDR3 of M0162-A04, the HC CDR3 of DX-2930 includes the variations of T101I, I103V, and A108E (see Table 2 below; the HC CDR3 of DX-2930 being identical to M0199-A08). The Chothia Numbering Scheme is used in the present disclosure. www.bioinf.org.uk/abs/.

Table 1 below provides structural information of DX-2930, its parent antibody M0162-A04, and variants thereof. See also US20120201756 and US20110200611.

TABLE 1

Structural Properties of DX-2930 and Related Variants

| Name | Properties |
|---|---|
| M162-A04 | This is the parent antibody of DX-2930 that was discovered in the initial phage display selection efforts (Ki, app = 2.5 nM). This antibody differs from DX-2930 at 3 critical amino acids in the CDR3 of the heavy chain and the germlined positions. |
| M199-A08 | Fab discovered following the affinity maturation of M0162-A04 using the Hv-CDR3 spiking method (Ki, app~0.06 nM). This antibody shares the same amino acids in the variable region with DX-2930 but was not germlined and does not contain a Fc fragment. |
| X115-F02 | Fully human IgG, kappa light chain 1 amino acid in the light chain was mutated to their germline sequence. The DNA sequence of X115-F02 was optimized for expression in CHO cells Expressed transiently in 293T cells following subcloning into the pRH1-CHO vector |
| DX-2930 (X124-G01) | Fully human IgG, kappa light chain 1 amino acid in the light chain and 2 amino acids in the heavy were mutated to their germline sequence. The DNA sequence of DX-2930 was optimized for expression in CHO cells and cloned into the pEh1 vector for stable expression using the glutamate synthase system. The Fc of DX-2930 was modified to remove the C-terminal lysine reside, in order to obtain a more homogeneous product. |

Crystal structures (with different resolutions) of a complex formed between the Fab fragment of DX-2930 and the catalytic domain of human plasma kallikrein (PKal) was determined. Based on the structural information provided by the crystal structures, a number of interacting residues in both the catalytic domain of human PKal and the antibody (in both $V_H$ and $V_L$) were identified. The interacting residues in the PKal are important targets for developing antibodies capable of inhibiting the PKal activity. Similarly, the interacting residues in the antibody also provide important structural information for designing anti-PKal antibodies with high inhibitory activity.

Further, affinity maturation analysis was performed to develop high affinity anti-PKal antibodies, using clone M0162-A04 as the parent. Results obtained from affinity maturation matches with the structural information provided by the crystal structures. Based on the structural information and the affinity maturation results, specific VH and VL motifs/residues were identified for designing anti-PKal antibodies with high inhibitory activities.

Accordingly, described herein are antibodies capable of binding to plasma kallikrein (e.g., human plasma kallikrein; PKal) and inhibiting its activity, and uses thereof for treating diseases and disorders associated with plasma kallikrein. Such antibodies interact with one or more critical residues in the catalytic domain of the PKal and/or comprise specific motifs/residues in either the heavy chain variable region (e.g., HC CDR1 or HC CDR3) or the light chain variable region (e.g., LC CDR2), or both.

Antibodies Binding to PKal

The present disclosure provides isolated antibodies that bind PKal, particularly the catalytic domain of the PKal, such as human PKal. The term "isolated antibody" used herein refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies described herein are capable of binding to a PKal, particularly the catalytic domain of a PKal (e.g., human PKal), thereby inhibiting the activity of PKal. In some instances, the antibodies described herein can inhibit the activity of PKal by at least 50%, e.g., 60%, 70%, 80%, 90%, 95%, or higher. The inhibition constant (Ki) provides a measure of inhibitor potency; it is the concentration of inhibitor required to reduce enzyme activity by half and is not dependent on enzyme or substrate concentrations. The inhibitory activity of an anti-PKal antibody can be determined by routine methods, such as the method described in Example 2 below.

In some examples, the inhibitory activity of an anti-PKal antibody is determined by the apparent Ki ($K_{i,app}$) value. The $K_{i,app}$ value of an antibody obtained at different substrate concentrations by measuring the inhibitory effect of different concentrations of the antibody on the extent of the reaction (e.g., enzyme activity); fitting the change in pseudo-first order rate constant as a function of inhibitor concentration to the Morrison equation (Equation 1) yields an estimate of the apparent Ki value. For a competitive inhibitor, the Ki is obtained from the y-intercept extracted from a linear regression analysis of a plot of $K_{i,app}$ versus substrate concentration.

$$v = v_o - v_o\left(\frac{(K_{i,app} + I + E) - \sqrt{(K_{i,app} + I + E)^2 - 4 \cdot I \cdot E}}{2 \cdot E}\right) \quad \text{Equation 1}$$

In some examples, the anti-PKal antibodies described herein have a $K_{i,app}$ value lower than 1 nM, e.g., 0.5 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, or lower. The $K_{i,app}$ value of an antibody can be estimated following the methods known in the art and described herein (Example 2).

The antibodies described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-PKal antibodies described herein have a suitable binding affinity to a PKal or the catalytic domain thereof. As used herein, "binding affinity" refers to the apparent association constant or $K_A$. The $K_A$ is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

[Bound]=[*N*][Free]/(*Kd*+[Free])

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

Antibodies Targeting Specific Residues in Human Plasma Kallikrein

In some embodiments, the anti-PKal antibodies interact with one or more of the residues (e.g., at least 3, 5, 8, 10, 15, 20, 25, 30, 35, 40, or 45) in the catalytic domain of human PKal, including V410, L412, T413, A414, Q415, R416, L418, C419, H434, C435, F436, D437, G438, L439, W445, Y475, K476, V477, S478, E479, G480, D483, F524, E527, K528, Y552, D554, Y555, A564, D572, A573, C574, K575, G576, S578, T596, S597, W598, G599, E600, G601, C602, A603, R604, Q607, P608, G609, V610, and Y611 (numbers based on the full length prekallikrein amino acid sequence). The positions of these residues are indicated in FIG. 2 (boldfaced and underlined). These residues are identified as important to the pKal activity, according to the crystal structures described in Example 1 below.

In some embodiments, the anti-PKal antibodies interact with one or more of the residues (e.g., at least 3, 5, 8, 10, 15, 20, or 23) in the catalytic domain of human PKal, including L418, C419, H434, C435, D437, G438, L439, Y475, D483, F524, D572, A573, C574, K575, G576, S578, T596, S597, W598, G599, E600, G601, and C602 (numbers based on the full length prekallikrein amino acid sequence).

In some embodiments, the anti-PKal antibodies interact with one or more of the residues (e.g., at least 3, 5, or 8) in the catalytic domain of human PKal, including K476, V477, S478, E479, G480, Y552, D554, and Y555 (numbers based on the full length prekallikrein amino acid sequence).

In some embodiments, the anti-PKal antibodies interact with one or more of the residues (e.g., at least 3, 5, 8, or 10) in the catalytic domain of human PKal, including V410, L412, T413, A414, Q415, R416, E527, K528, A603, and R604 (numbers based on the full length prekallikrein amino acid sequence).

In some embodiments, the anti-PKal antibodies interact with one or more of the residues (e.g., at least 3, 5, or 6) in the catalytic domain of human PKal, including W445, Q607, P608, G609, V610, and Y611 (numbers based on the full length prekallikrein amino acid sequence).

In some embodiments, the anti-PKal antibodies interact with one or more of the residues (e.g., at least 3, 5, 8, or 9) in the catalytic domain of human PKal, including F524, D572, A573, C574, K575, G576, S578, G601, and C602 (numbers based on the full length prekallikrein amino acid sequence).

In some embodiments, the anti-PKal antibodies interact with one or more of the residues (e.g., at least 3, 5, or 8) in the catalytic domain of human PKal, including L418, C419, H434, C435, D437, G438, Y475, and D483 (numbers based on the full length prekallikrein amino acid sequence).

In some embodiments, the anti-PKal antibodies interact with one or more of the residues (e.g., at least 3 or 4) in the catalytic domain of human PKal, including S597, W598, G599, and E600 (numbers based on the full length prekallikrein amino acid sequence).

Interacting means that the distance between two residues in a complex formed by two binding partners is lower than a predetermined value, e.g., <6 Å, <4 Å, or <2 Å. For example, an interacting residue in one binding partner can have has at least 1 atom within a given threshold (e.g., <6 Å, <4 Å, or <2 Å) of at least 1 atom from a residue of the other binding partner on the complexed structure. Interacting does not require actual binding. Interacting residues are suggested as involved in antibody recognition.

In some embodiments, the antibodies described herein bind human PKal at an epitope comprising one or more of the residues listed above. An "epitope" refers to the site on a target compound that is bound by an antibody such as a Fab or full length antibody. An epitope can be linear, which is typically 6-15 aa in length. Alternatively, the epitope can be conformational.

In some examples, the anti-PKal antibodies described herein binds an epitope that comprises the following segments: V410-C419, H434-L439, Y475-G480, F524-K528, Y552-Y555, D572-S578, T596-R604, or Q607-Y611.

In some examples, the antibody disclosed herein specifically binds PKal or an epitope therein. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to human PKal or an epitope therein is an antibody that binds this target antigen with greater affinity, avidity, more readily, and/or with greater duration than it binds to other antigens or other epitopes in the same antigen. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

In one example, the anti-PKal antibodies described herein preferentially bind wild-type as compared to a mutant that includes mutations at one or more of R551, Q553, Y555, T558, and R560, e.g., Mutant 2 described in Example 3. Such antibodies may bind wild-type PKal at a much higher affinity as compared to the mutant (e.g., at least 2-fold, 5-fold, 10-fold, 50-fold, 100-fold, 200-fold, 500-fold, 1,000-fold higher). Alternatively or in addition, the antibodies exhibit a much higher inhibitory activity against the wild-type pKal as relative to the mutant (e.g., at least 2-fold, 5-fold, 10-fold, 50-fold, 100-fold, 200-fold, 500-fold, 1,000-fold higher).

In other examples, the anti-PKal antibodies described herein binds active PKal, including wild-type pKal and functional variant thereof. The antibody can preferentially bind an active PKal as relative to its binding to an inactive mutant.

Anti-Plasma Kallikrein Antibodies Having Specific Motifs and/or Residues

In some embodiments, the anti-PKal antibody described herein comprises a $V_H$ and a $V_L$, each of which comprises three CDRs flanked by framework regions (FR1-CDR1-FR2-CDR2-FR3-CDR3-FR4; see FIG. 1). The CDR3 of the heavy chain can comprise the motif: $X_{99}R_{100}X_{101}G_{102}X_{103}P_{104}R_{105}X_{106}X_{107}X_{108}X_{109}X_{110}X_{111}$, in which $X_{99}$ is R or Q, $X_{101}$ is T, I, R, S, or P, $X_{103}$ is V, I, or L, $X_{106}$ is R or W, $X_{107}$ is D or N, $X_{108}$ is A, S, D, E, or V, $X_{109}$ is F or L, $X_{110}$ is D, E, or N, and $X_{111}$ is I, N, M, or S. In some examples, $X_{99}$ is Q and $X_{101}$ is I, R, S, or P. Alternatively or in addition, $X_{106}$ is W and $X_{111}$ is N, M, or S. In other examples, $X_{101}$ is I, $X_{108}$ is E, and $X_{103}$ is I or L; or $X_{101}$ is I and $X_{103}$ is I or L. In yet other examples, $X_{103}$ is I or L and $X_{110}$ is D, E, or N.

In addition, such an anti-pKal antibody can include one or more other residues that are identified based on the crystal structures discussed herein as being involved in interacting with the catalytic domain of human PKal. These residues can be located in the $V_H$ or the $V_L$ chain. Examples include E1, V2, F27, T28, F29, and S30 in the FR1 of the $V_H$, $H_{31}$ in the HC CDR1; S31 and W32 in the LC CDR1, Y49 in the FR1 of the $V_L$ chain, K50, T53, L54, and E55, and S56 in LC CDR2, and G57 and V58 the FR3 of the $V_L$ chain.

The anti-PKal antibodies as described above can use any germline heavy chain and light chain V genes as the framework. Heavy chain V genes include, but are not limited to, IGHV1-2, IGHV1-3, IGHV1-8, IGHV1-18, IGHV1-24, IGHV1-45, IGHV1-46, IGHV1-58, IGHV1-69, IGHV2-5, IGHV2-26, IGHV2-70, IGHV3-7, IGHV3-9, IGHV3-11, IGHV3-13, IGHV3-15, IGHV3-20, IGHV3-21, IGHV3-23, IGHV3-30, IGHV3-33, IGHV3-43, IGHV3-48, IGHV3-49, IGHV3-53, IGHV3-64, IGHV3-66, IGHV3-72, IGHV3-73, IGHV3-74, IGHV4-4, IGHV4-28, IGHV4-31, IGHV4-34, IGHV4-39, IGHV4-59, IGHV4-61, IGHV4-B, IGHV5-51, IGHV6-1, and IGHV7-4-1.

In some examples, the antibody uses a κ light chain. Light chain VK genes include, but are not limited to, V genes for IGKV1-05, IGKV1-06, IGKV1-08, IGKV1-09, IGKV1-12, IGKV1-13, IGKV1-16, IGKV1-17, IGKV1-27, IGKV1-33, IGKV1-37, IGKV1-39, IGKV1D-16, IGKV1D-17, IGKV1D-43, IGKV1D-8, IGKV2-24, IGKV2-28, IGKV2-29, IGKV2-30, IGKV2-40, IGKV2D-26, IGKV2D-29, IGKV2D-30, IGKV3-11, IGKV3-15, IGKV3-20, IGKV3D-07, IGKV3D-11, IGKV3D-20, IGKV4-1, IGKV5-2, IGKV6-21, and IGKV6D-41. In other examples, the antibody uses a λ light chain, e.g., any of IGLV1-IGLV10.

The antibody also can use any germline heavy J segment (e.g., heavy chain IGJH1-IGJH6) and light chain J segment (e.g., IGJK1, IGJK2, IGJK3, IGJK4, or IGJK5), which can subject to variations, such as deletions at the C-terminus, N-terminus, or both.

Germline antibody gene/segment sequences are well known in the art. See, e.g., www.vbase2.org/vbstat.php.

In some examples, the anti-PKal antibody described herein uses VH3_3-23 and/or VK1_L12 as the framework for the heavy chain and/or the light chain. It may include substantially similar HC CDR1, HC CDR2, and/or HC CDR3, and LC CDR1, LC CDR2, and/or LC CDR3 as those in M0162-A04 (FIG. 1), e.g., containing up to 5, 4, 3, 2, or 1 amino acid residue variations as compared to the corresponding CDR region in M0162-A04.

In other examples, the anti-PKal antibody comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of M0162-A04, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_L$ CDRs of M0162-A04.

Alternatively, the anti-PKal antibody comprises a $V_H$ chain at least 75% (e.g., 80%, 85%, 90%, 95%, or 98%) identical to the $V_H$ chain (mature or precursor) of M0162-A04 and/or a $V_L$ chain at least 75% (e.g., 80%, 85%, 90%, 95%, or 98%) identical to the $V_L$ chain (mature of precursor) of M0162-A04.

The "percent identity" of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some instances, conservative mutations can be introduced into the CDRs in M0162-A04, e.g., at positions where the residues are not likely to be involved in interacting with PKal as determined based on the crystal structure. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the anti-PKal antibodies described here are not those described in US 20110200611, which is incorporated by reference herein.

In some embodiments, the anti-PKal antibodies described herein bind to the same epitope as DX-2930 and/or compete for binding with DX-2930, with the proviso that the anti-PKal antibody is not DX-2930. In some embodiments, the anti-Pkal antibodies described herein bind to the sequence SWGE (SEQ ID NO: 48) and/or DACKG (SEQ ID NO: 49) in PKal. In some embodiments, the anti-Pkal antibodies described herein do not bind to the sequence SWGE (SEQ ID NO: 48) and/or DACKG (SEQ ID NO: 49) in Pkal. In some embodiments, the anti-Pkal antibodies described herein bind to the sequence DGL, SEG, TSWGEG (SEQ ID NO: 50) and/or DACKG (SEQ ID NO: 49) in Pkal. In some embodiments, the anti-Pkal antibodies described herein do not bind to the sequence DGL, SEG, TSWGEG (SEQ ID NO: 50) and/or DACKG (SEQ ID NO: 49) in Pkal. In some embodiments, the anti-Pkal antibodies described herein do not bind to the sequence

```
                            (SEQ ID NO: 51)
LVTNEECQKRYQDYKITQQ, (SEQ ID NO: 52)
WVTGWGFSKEKGEI, (SEQ ID NO: 53)
ACKGDSGGPL,
```

```
                            (SEQ ID NO: 54)
SWGDI, (SEQ ID NO: 55)
HDIALIKL, (SEQ ID NO: 56)
TPFSQIKEIIIHQNY,
and/or (SEQ ID NO: 57)
AHCFDGLPLQDVWRIY.
```

In some embodiments, the anti-PKal antibody described herein binds to an epitope located in the active domain of PKal (the whole epitope or a portion thereof) and is different from that DX-2930. The epitope of such an antibody may have overlapping residues with those of the epitope of DX-2930. Alternatively, there can be no overlapping residues between the two epitopes.

The sequences of the full length heavy chain and light chain of DX-2930 are shown below.

```
DX-2930 Heavy Chain Amino Acid Sequence (451 amino acids)
                            (SEQ ID NO: 46)
EVQLLESGGGLVQPGGSLRLSCAASGFTFSHYIMMWVRQAPGKGLEWVSGIYSSGGITVYAD

SVKGRFTISRDNSKNTLYLQMNSLRAEDTAVYYCAYRRIGVPRRDEFDIWGQGTMVTVSSAS

TKGPSVFPLAPSSKSTSGGTAALGCLVKDYFPEPVTVSWNSGALTSGVHTFPAVLQSSGLYS

LSSVVTVPSSSLGTQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSREEMTKNQVSLTC

LVKGFYPSDIAVEWESNGQPENNYKTTPPVLDSDGSEELYSKLTVDKSRWQQGNVFSCSVMH

EALHNHYTQKSLSLSPG

DX-2930 Light Chain Amino Acid Sequence (213 amino acids)
                            (SEQ ID NO: 47)
DIQMTQSPSTLSASVGDRVTITCRASQSISSWLAWYQQKPGKAPKLLIYKASTLESGVPSRF

SGSGSGTEFTLTISSLQPDDFATYYCQQYNTYWTFGQGTKVEIKRTVAAPSVFTFPPSDFQL

KSGTASVVCLLNNFYPREAKVQWKVDNALQSGNSQESVTEQDSKDSTYSLSSTLTLSKADYE

KHKVYACEVTHQGLSSPVTKSFNRGEC
```

In the above sequences, the constant regions are italicized and the CDR regions are in boldface and underlined.

Antibody Preparation

Antibodies capable of binding PKal as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., a human PKal or the catalytic domain thereof) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-PKal monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the PKal activity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of PKal. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455, and. Alternatively, the phage display technology (McCafferty et al., (1990) Nature 348: 552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to a PKal can be identified from the library following routine procedures. Positive clones can be subjected to further screening to identify those that inhibits PKal activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the PKal polypeptide have been replaced (swapped) with sequences from a closely related, but antigenically distinct protein (such as another member of the neurotrophin protein family). By assessing binding of the antibody to the mutant PKal (e.g., those mutants described in Example 2 below), the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Any of the suitable methods known in the art, e.g., the epitope mapping methods as described herein, can be applied to determine whether the anti-PKal antibody binds one or more of the specific residues/segments in the PKal as described herein. Further, the interaction of the antibody with one or more of those defined residues in PKal can be determined by routine technology. For example, a crystal structure can be determined following the method disclosed in Example 1 below and the distances between the residues in PKal and one or more residues in the antibody can be determined accordingly. Based on such distance, whether a specific residue in PKal interacts with one or more residues in the antibody can be determined. Further, suitable methods, such as competition assays and target mutagenesis assays can be applied to determine the preferential binding of a candidate anti-PKal antibody to the PKal as compared to another target such as a mutant PKal.

Pharmaceutical Compositions

One or more of the above-described anti-PKal antibodies can be mixed with a pharmaceutically acceptable carrier (excipient), including buffer, to form a pharmaceutical composition for use in alleviating a disease or disorder that is associated with PKal. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. In one example, a pharmaceutical composition described herein contains more than one anti-PKal antibodies that recognize different epitopes/residues of the target antigen.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the anti-PKal antibody, which can be prepared by methods known in the art, such as described in Epstein, et al., *Proc. Natl. Acad. Sci.* USA 82:3688 (1985); Hwang, et al., *Proc. Natl. Acad. Sci.* USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-PKal antibody may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(v nyl-alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation. For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0.im, particularly 0.1 and 0.5.im, and have a pH in the range of 5.5 to 8.0.

The emulsion compositions can be those prepared by mixing an anti-PKal antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Use of Anti-PKal Antibodies for Treating Diseases/Disorders Associated with Plasma Kallikrein The anti-PKal antibodies described herein would be effective in treating a disease or disorder associated the PKal. Examples of such diseases and conditions which can be treated (or prevented) by a plasma kallikrein binding protein described herein include: rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edema, hereditary angioedema, cerebral edema, pulmonary embolism, stroke, clotting induced by ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis, burn injury, and DME. A plasma kallikrein binding protein described herein can also be used to promote wound healing. A plasma kallikrein binding protein described herein can also be used as an oncology treatment by mechanisms that include, but are not limited to, blocking production of pro-angiogenic bradykinin.

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-PKal antibodies can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a disease/disorder associated with PKal, such as those noted above. A subject having a PKal-associated disease or disorder can be identified by routine medical examination, e.g., laboratory tests, organ functional tests, CT scans, or ultrasounds. A subject suspected of having any of such disease/disorder might show one or more symptoms of the disease/disorder. A subject at risk for the disease/disorder can be a subject having one or more of the risk factors for that disease/disorder.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a disease/disorder associated with PKal. Alternatively, sustained continuous release formulations of an anti-PKal may be appropriate. Various formulations and devices for achieving sustained release are known in the art.

In one example, dosages for an anti-PKal antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a disease or disorder associated with PKal, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 g/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an anti-PKal antibody will depend on the specific antibody (or compositions thereof) employed, the type and severity of the disease/disorder, whether the antibody is administered for preventive or therapeutic purposes, previous therapy, the patient's clinical history and response to the antagonist, and the discretion of the attending physician. Typically the clinician will administer an anti-PKal antibody, until a dosage is reached that achieves the desired result. Administration of an anti-PKal antibody can be continuous or intermittent, depending, for example, upon the recipient's physiological condition, whether the purpose of the administration is therapeutic or prophylactic, and other factors known to skilled practitioners. The administration of an anti-PKal antibody may be essentially continuous over a preselected period of time or may be in a series of spaced dose, e.g., either before, during, or after developing a disease or disorder associated with PKal.

As used herein, the term "treating" refers to the application or administration of a composition including one or more active agents to a subject, who has a disease/disorder associated with PKal, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease/disorder.

Alleviating a disease/disorder associated with PKal includes delaying the development or progression of the disease, or reducing disease severity. Alleviating the disease does not necessarily require curative results. As used therein, "delaying" the development of a disease/disorder associated with PKal means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease/disorder associated with PKal includes initial onset and/or recurrence.

In some embodiments, the anti-PKal antibody described herein is administered to a subject in need of the treatment at an amount sufficient to inhibit the activity of PKal by at least 20% (e.g., 30%, 40%, 50%, 60%, 70%, 80%, 90% or greater) in vivo. In other embodiments, the antibody is administered in an amount effective in reducing the PKal level by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an anti-PKal antibody is administered via site-specific or targeted local delivery techniques. Examples of site-specific or targeted local delivery techniques include various implantable depot sources of the anti-PKal antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapetics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the anti-PKal antibodies described herein) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698;

WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history. In some embodiments, more than one anti-PKal antibodies, or a combination of an anti-PKal antibody and another suitable therapeutic agent, may be administered to a subject in need of the treatment. The antagonist can be the same type or different from each other. The anti-PKal antibody can also be used in conjunction with other agents that serve to enhance and/or complement the effectiveness of the agents.

Treatment efficacy for a disease/disorder associated with PKal can be assessed by methods well-known in the art.

Kits for Use in Alleviating Diseases/Disorders Associated with Plasma Kallikrein The present disclosure also provides kits for use in alleviating diseases/disorders associated with plasma kallikrein. Such kits can include one or more containers comprising an anti-PKal antibody, e.g., any of those described herein.

In some embodiments, the kit can comprise instructions for use in accordance with any of the methods described herein. The included instructions can comprise a description of administration of the anti-PKal antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of an anti-PKal antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with PKal. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-PKal antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Identification of Critical Residues in the Catalytic Domain of Human Plasma Kallikrein Based on Crystal Structures of DX-2930-PKal Complex The catalytic domain of human plasma kallikrein (FIG. 2), fused with a His-tag, was expressed in insect cells and purified initially by a nickel affinity column. The His-tag was removed from the plasma kallikrein via trypsin digestion and the free plasma kallikrein was purified by a benzamidine affinity column, followed by a SEC column. The purified product was examined on a PAGE gel. The result indicates that the catalytic domain of human plasma kallikrein was properly expressed and purified.

DX-2930 was prepared via routine recombinant technology and purified. A recombinant Fab fragment of DX-2930 was produced via routine method and purified.

The DX-2930 Fab fragment and the catalytic domain of human plasma kallikrein were mixed at various concentrations under suitable conditions allowing formation of antibody-PKal complexes. The complexes thus formed were examined using HPLC to determine the antibody-PKal ratio in the complexes. Accordingly, the suitable concentrations of both the antibody and the PKal were identified for formation of a 1:1 complex.

The antibody-PKal complex was kept under various conditions allowing for crystallization. Diffraction analysis was performed on the crystallized complex. The crystal structures (2.1 Å and 2.4 Å) were determined based on the diffraction statistics.

According to the crystal structures, residues in the catalytic domain of human Pkal that are involved in the interaction with DX-2930 were identified. These residues are indicated (boldfaced and underlined) in FIG. 2, which provides the amino acid sequence of the catalytic domain of human PKal (residues 391-638 of human PKal).

In addition, residues in DX-2930 that interact with PKal were also identified based on the crystal structure, including E1, V2, F27, T28, F29, S30, H31, R100, I101, G102, V103, P104, R105, R106, D107, G107, K108, and D111 in the heavy chain variable region, and S31, W32, Y49, K50, T53, L54, E55, S56, G57, and V58 in the light chain variable region.

These results indicate that HC CDR3 of DX-2930 is the main region that interacts with PKal (see FIG. 1) and a couple of residues in the HC CDR1 and FR1 might also contribute to the interaction with PKal. In the light chain, the LC CDR2 region was found to contribute to the interaction.

Further, the results also indicate that variations at certain positions with the HC CDR3 region may be allowed. For example, position 103 requires small hydrophobic residues such as V or I. As another example, R106 may be replaced with W, and E108 may be replaced with S or D without substantially affecting the PKal binding activity. Similarly, D110 might be replaced with E.

Example 2: Affinity Maturation Results Match Structural Information Derived from Crystal Structure The heavy chain variable region, particularly the HC CDR3 region, of antibody M0162-A04 was subject to affinity maturation. Various mutants having amino acid variations at one or more positions in the HC CDR3 region were generated and their $K_{i,app}$ values were determined following routine methods.

Briefly, PKal and a Fab at various concentrations are incubated together for 1 hour at 30° C. A substrate peptide (cleavable by PKal) is then added to this PKal-Fab mixture. The rate of substrate peptide cleavage/proteolysis is then measured, and plotted against the concentrations of the Fab. This plot is then fit to the Morrison equation, which calculates the $K_{i,app}$ value. The results thus obtained are shown in FIG. 3 and Table 2 below:

TABLE 2

Summary of Hv-CDR3 Affinity Maturation Results

| Initial Name | Hv CDR3 | Ki, app (nM) | SEQ ID NO |
|---|---|---|---|
| M0162-A04 | RRTGIPRRDAFDI | 2.5 | 1 |
| M0199-A11 | --R---------- | 2 | 2 |
| M0201-F11 | --S---------- | 3 | 3 |
| M0202-A08 | -------W----- | 2.8 | 4 |
| M0201-A06 | ---------V--- | 3.8 | 5 |
| M0202-E03 | -----------E- | 2 | 6 |
| M0199-B01 | ------------N | 1.6 | 7 |
| M0200-B01 | ------------S | 3.6 | 8 |
| M0201-H06 | ----V-------- | 0.6 | 9 |
| M0202-H05 | ----V----V--- | 0.26 | 10 |
| M0201-H08 | ----V-----L-N | 0.8 | 11 |
| M0200-E11 | ----V-------N | 0.4 | 12 |
| M0200-H07 | ----V---N---N | 0.4 | 13 |
| M0202-F06 | ----V--W----- | 0.33 | 14 |
| M0200-A10 | ----V----S--- | 0.25 | 15 |
| M0202-G03 | ----V----S-E- | 0.4 | 16 |
| M0202-A12 | Q---V----S-N- | 0.1 | 17 |
| M0202-H03 | ----V--W-D--- | 0.1 | 18 |
| M0201-A07 | ----V----E--- | 0.1 | 19 |
| M0202-C02 | --P-V-------- | 0.6 | 20 |
| M0202-B04 | --S-V-------- | 0.2 | 21 |
| M0202-E06 | --R-V----D--- | 0.06 | 22 |
| M0202-A01 | --I-V-------- | 0.3 | 23 |
| M0202-D09 | --I-V----S--- | 0.2 | 24 |
| M0200-D03 | --I-V----S--M | 0.1 | 25 |
| M0202-C09 | --I-V----D--- | 0.06 | 26 |
| M0199-A08 | --I-V----E--- | 0.06 | 27 |
| X133-B02 | --I---------- | 2.2 | 28 |
| X133-D06 | --I------E--- | 0.33 | 29 |
| X135-A01 | ----A-------- | 247.7 | 30 |

TABLE 2-continued

Summary of Hv-CDR3 Affinity Maturation Results

| Initial Name | Hv CDR3 | Ki, app (nM) | SEQ ID NO |
|---|---|---|---|
| X133-G05 | ----S-------- | 1405.6 | 31 |
| X133-F10 | ----L-------- | 14.7 | 32 |
| X135-A03 | ---------E--- | 1.1 | 33 |

The affinity maturation results indicate that variations at certain positions within the HC CDR3 region result in high affinity/inhibitory anti-PKal antibodies as compared to the parent M0162-A04 clone. These results match with the structural information provided in Example 1 above. Note that the HC CDR3 region of clone M0199-AOS is identical to that of DX-2930.

Example 3: Impact of Mutations in Plasma Kallikrein on Antibody Inhibitory Activity The inhibitory activities of mutant X115-F02 against various PKal mutants were examined.

X115-F02 is an IgG that is the same as DX-2930 except that it contains a C-terminal lysine residue not present in DX-2930 and was expressed in HEK293T cells rather than CHO cells (Table 1 above). The binding specificity and affinity of X115-F02 is the same as DX-2930.

The wild type and four mutants of plasma kallikrein used in this study (FIG. 5) are recombinant catalytic domains expressed and purified from *Pichia pastoris*. Mutant 1 contains the following mutations in the S3 subsite of the active site: S478A, N481A, S506A, Y507A) (numbers based on the full length prekallikrein amino acid sequence). Mutant 2 contains the following mutations in the S1' subsite of the active site: R551A, Q553A, Y555A, T558A, R560A. Mutant 4 contains the following mutations that are distal from the active site: N396A, S398A, W399A. Mutant 3 was found to be inactive and therefore was not tested in the activity assay. Mutant 3 contains the following mutations in the S1' subsite of the active site: D572A, K575A, D577A.

Figure 4:
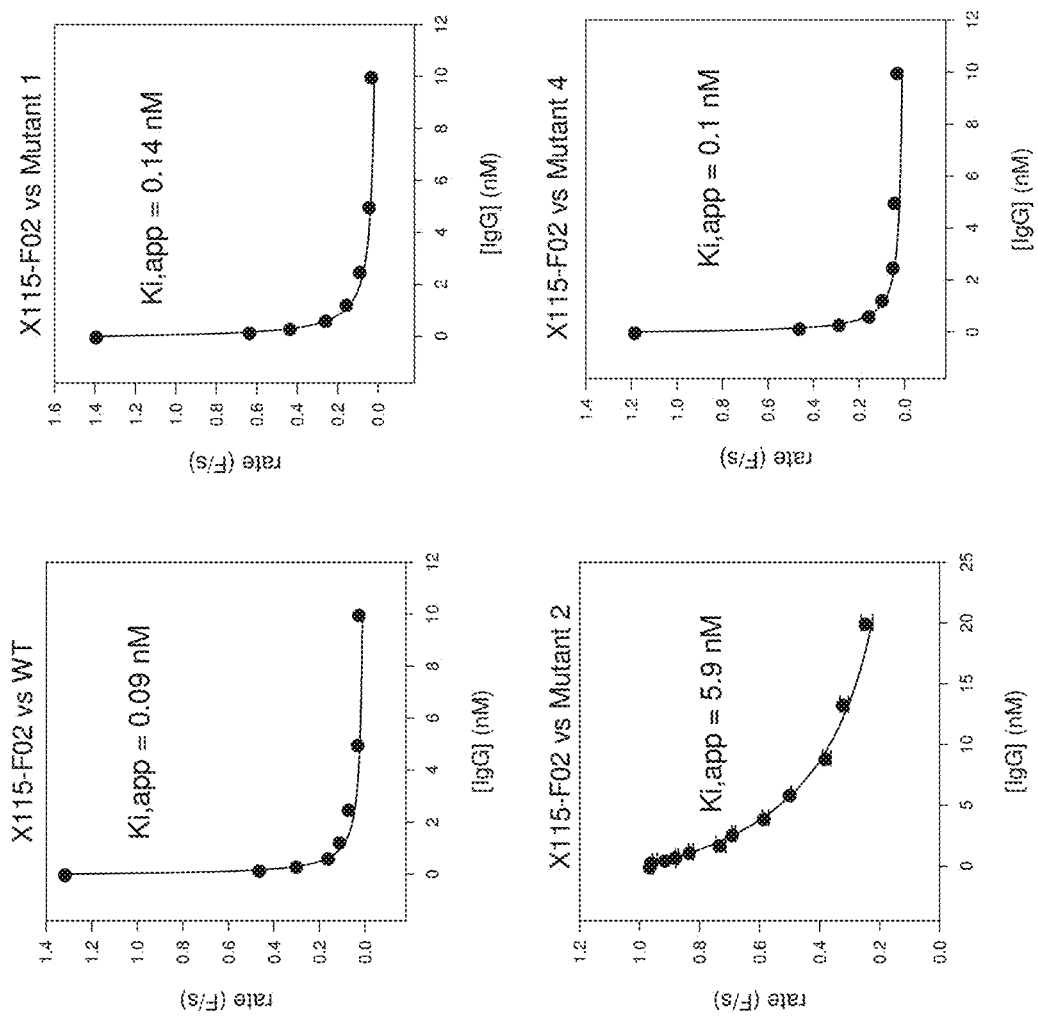
FIG. 4 is a graph showing the apparent Ki ($K_{i, app}$) of clone X115-F02 (see Table 1 below) against wild-type PKal and a number of PKal mutants.

The inhibitory activity of X115-F02 against the wild-type PKal and the mutants were carried out using the method described in Example 2 above and the $K_{i,app}$ values were determined. As shown in FIG. 4, the mutations in Mutant 1 and 4 did not significantly affect the potency of X115-F02 inhibition of plasma kallikrein. Surprisingly, the mutations in Mutant 2 reduced the potency approximately 65-fold. These results indicate that residues R551A, Q553A, Y555A, T558A, R560A and their adjacent residues might be important to the inhibitory activity of X115-F02 (DX-2930).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for inhibiting plasma kallikrein (pKal) activity, comprising administering to a subject an effective amount of an antibody that binds pKal, wherein the antibody comprises:

a heavy chain variable region that comprises a complementarity determining region 1 (HC CDR1) comprising the sequence HYIMM (SEQ ID NO: 62), a complementarity determining region 2 (HC CDR2) comprising the sequence GIYSSGGITVYADSVKG (SEQ ID NO: 63), and a complementarity determining region 3 (HC CDR3) comprising the sequence (HC CDR3) comprising the sequence (i)
                                    (SEQ ID NO: 28)
RRIGIPRRDAFDI;

(ii)
                                    (SEQ ID NO: 29)
RRIGIPRRDEFDI;

(iii)
                                    (SEQ ID NO: 30)
RRTGAPRRDAFDI;

(iv)
                                    (SEQ ID NO: 31)
RRTGSPRRDAFDI;

(v)
                                    (SEQ ID NO: 32)
RRTGLPRRDAFDI;
or (vi)
                                    (SEQ ID NO: 33)
RRTGIPRRDEFDI;
and a light chain (LC) variable region that comprises a complementarity determining region 1 (LC CDR1) comprising the sequence RASQSISSWLA (SEQ ID NO: 59), a complementarity determining region 2 (LC CDR2) comprising the sequence KASTLES (SEQ ID NO: 60), and a complementarity determining region 3 (LC CDR3) comprising the sequence QQYNTYWT (SEQ ID NO: 61).

2. The method of claim 1, wherein the antibody is a full-length antibody or an antigen-binding fragment thereof.

3. The method of claim 2, wherein the antibody is an IgG.

4. The method of claim 1, wherein the antibody is a human antibody or a humanized antibody.

5. The method of claim 1, wherein the antibody inhibits the activity of pKal by at least 80%.

6. The method of claim 1, wherein the antibody has a $K_{i,app}$ lower than about 1 nM.

7. The method of claim 1, wherein the light chain variable region further comprises $G_{57}$ in the framework region 3 (FR3) with respect to the amino acid sequence of SEQ ID NO: 34.

8. The method of claim 1, wherein the light chain variable region further comprises $N_{45}$ in the framework region 2 (FR2) with respect to the amino acid sequence of SEQ ID NO: 34.

9. The method of claim 1, wherein the antibody preferentially binds an active pKal.

10. The method of claim 1, wherein the subject is a human patient diagnosed with a disease, wherein the disease is rheumatoid arthritis, gout, intestinal bowel disease, oral mucositis, neuropathic pain, inflammatory pain, spinal stenosis, arterial or venous thrombosis, post-operative ileus, aortic aneurysm, osteoarthritis, vasculitis, edema, hereditary angioedema, cerebral edema, pulmonary embolism, stroke, clotting induced by ventricular assistance devices or stents, peri-tumor brain edema, sepsis, acute middle cerebral artery ischemic event, restenosis, systemic lupus erythematosus nephritis, or diabetic macular edema.

* * * * *

SEQUENCE LISTING

```
<160> NUMBER OF SEQ ID NOS: 64

<210> SEQ ID NO 1
<211> LENGTH: 13
<212> TYPE: PRT
<213> ORGANISM: Artificial sequence
<220> FEATURE:
<223> OTHER INFORMATION: Hv-CDR3

<400> SEQUENCE: 1

Arg Arg Thr Gly Ile Pro Arg Arg Asp Ala Phe Asp Ile
1               5                   10

<210> SEQ ID NO 2
<211> LENGTH: 13
<212> TYPE: PRT
<213> ORGANISM: Artificial sequence
<220> FEATURE:
<223> OTHER INFORMATION: Hv-CDR3

<400> SEQUENCE: 2

Arg Arg Arg Gly Ile Pro Arg Arg Asp Ala Phe Asp Ile
1               5                   10

<210> SEQ ID NO 3
<211> LENGTH: 13
<212> TYPE: PRT
<213> ORGANISM: Artificial sequence
<220> FEATURE:
<223> OTHER INFORMATION: Hv-CDR3
```

<400> SEQUENCE: 3

Arg Arg Ser Gly Ile Pro Arg Arg Asp Ala Phe Asp Ile
1               5                   10

<210> SEQ ID NO 4
<211> LENGTH: 13
<212> TYPE: PRT
<213> ORGANISM: Artificial sequence
<220> FEATURE:
<223> OTHER INFORMATION: Hv-CDR3

<400> SEQUENCE: 4

Arg Arg Thr Gly Ile Pro Arg Trp Asp Ala Phe Asp Ile
1               5                   10

<210> SEQ ID NO 5
<211> LENGTH: 13
<212> TYPE: PRT
<213> ORGANISM: Artificial sequence
<220> FEATURE:
<223> OTHER INFORMATION: Hv-CDR3

<400> SEQUENCE: 5

Arg Arg Thr Gly Ile Pro Arg Arg Asp Val Phe Asp Ile
1               5                   10

<210> SEQ ID NO 6
<211> LENGTH: 13
<212> TYPE: PRT
<213> ORGANISM: Artificial sequence
<220> FEATURE:
<223> OTHER INFORMATION: Hv-CDR3

<400> SEQUENCE: 6

Arg Arg Thr Gly Ile Pro Arg Arg Asp Ala Phe Glu Ile
1               5                   10

<210> SEQ ID NO 7
<211> LENGTH: 13
<212> TYPE: PRT
<213> ORGANISM: Artificial sequence
<220> FEATURE:
<223> OTHER INFORMATION: Hv-CDR3

<400> SEQUENCE: 7

Arg Arg Thr Gly Ile Pro Arg Arg Asp Ala Phe Asp Asn
1               5                   10

<210> SEQ ID NO 8
<211> LENGTH: 13
<212> TYPE: PRT
<213> ORGANISM: Artificial sequence
<220> FEATURE:
<223> OTHER INFORMATION: Hv-CDR3

<400> SEQUENCE: 8

Arg Arg Thr Gly Ile Pro Arg Arg Asp Ala Phe Asp Ser
1               5                   10

<210> SEQ ID NO 9
<211> LENGTH: 13
<212> TYPE: PRT
<213> ORGANISM: Artificial sequence
<220> FEATURE:
<223> OTHER INFORMATION: Hv-CDR3

<400> SEQUENCE: 9

Arg Arg Thr Gly Val Pro Arg Arg Asp Ala Phe Asp Ile
1               5                   10

<210> SEQ ID NO 10
<211> LENGTH: 13
<212> TYPE: PRT
<213> ORGANISM: Artificial sequence
<220> FEATURE:
<223> OTHER INFORMATION: Hv-CDR3

<400> SEQUENCE: 10

Arg Arg Thr Gly Val Pro Arg Arg Asp Val Phe Asp Ile
1               5                   10

<210> SEQ ID NO 11
<211> LENGTH: 13
<212> TYPE: PRT
<213> ORGANISM: Artificial sequence
<220> FEATURE:
<223> OTHER INFORMATION: Hv-CDR3

<400> SEQUENCE: 11

Arg Arg Thr Gly Val Pro Arg Arg Asp Ala Leu Asp Asn
1               5                   10

<210> SEQ ID NO 12
<211> LENGTH: 13
<212> TYPE: PRT
<213> ORGANISM: Artificial sequence
<220> FEATURE:
<223> OTHER INFORMATION: Hv-CDR3

<400> SEQUENCE: 12

Arg Arg Thr Gly Val Pro Arg Arg Asp Ala Phe Asp Asn
1               5                   10

<210> SEQ ID NO 13
<211> LENGTH: 13
<212> TYPE: PRT
<213> ORGANISM: Artificial sequence
<220> FEATURE:
<223> OTHER INFORMATION: Hv-CDR3

<400> SEQUENCE: 13

Arg Arg Thr Gly Val Pro Arg Arg Asn Ala Phe Asp Asn
1               5                   10

<210> SEQ ID NO 14
<211> LENGTH: 13
<212> TYPE: PRT
<213> ORGANISM: Artificial sequence
<220> FEATURE:
<223> OTHER INFORMATION: Hv-CDR3

<400> SEQUENCE: 14

Arg Arg Thr Gly Val Pro Arg Trp Asp Ala Phe Asp Ile
1               5                   10

<210> SEQ ID NO 15
<211> LENGTH: 13
<212> TYPE: PRT
<213> ORGANISM: Artificial sequence
<220> FEATURE:
<223> OTHER INFORMATION: Hv-CDR3

<400> SEQUENCE: 15

```
Arg Arg Thr Gly Val Pro Arg Arg Asp Ser Phe Asp Ile
1               5                   10

<210> SEQ ID NO 16
<211> LENGTH: 13
<212> TYPE: PRT
<213> ORGANISM: Artificial sequence
<220> FEATURE:
<223> OTHER INFORMATION: Hv-CDR3

<400> SEQUENCE: 16

Arg Arg Thr Gly Val Pro Arg Arg Asp Ser Phe Glu Ile
1               5                   10

<210> SEQ ID NO 17
<211> LENGTH: 13
<212> TYPE: PRT
<213> ORGANISM: Artificial sequence
<220> FEATURE:
<223> OTHER INFORMATION: Hv-CDR3

<400> SEQUENCE: 17

Gln Arg Thr Gly Val Pro Arg Arg Asp Ser Phe Asn Ile
1               5                   10

<210> SEQ ID NO 18
<211> LENGTH: 13
<212> TYPE: PRT
<213> ORGANISM: Artificial sequence
<220> FEATURE:
<223> OTHER INFORMATION: Hv-CDR3

<400> SEQUENCE: 18

Arg Arg Thr Gly Val Pro Arg Trp Asp Asp Phe Asp Ile
1               5                   10

<210> SEQ ID NO 19
<211> LENGTH: 13
<212> TYPE: PRT
<213> ORGANISM: Artificial sequence
<220> FEATURE:
<223> OTHER INFORMATION: Hv-CDR3

<400> SEQUENCE: 19

Arg Arg Thr Gly Val Pro Arg Arg Asp Glu Phe Asp Ile
1               5                   10

<210> SEQ ID NO 20
<211> LENGTH: 13
<212> TYPE: PRT
<213> ORGANISM: Artificial sequence
<220> FEATURE:
<223> OTHER INFORMATION: Hv-CDR3

<400> SEQUENCE: 20

Arg Arg Pro Gly Val Pro Arg Arg Asp Ala Phe Asp Ile
1               5                   10

<210> SEQ ID NO 21
<211> LENGTH: 13
<212> TYPE: PRT
<213> ORGANISM: Artificial sequence
<220> FEATURE:
<223> OTHER INFORMATION: Hv-CDR3

<400> SEQUENCE: 21
```

Arg Arg Ser Gly Val Pro Arg Arg Asp Ala Phe Asp Ile
1               5                   10

<210> SEQ ID NO 22
<211> LENGTH: 13
<212> TYPE: PRT
<213> ORGANISM: Artificial sequence
<220> FEATURE:
<223> OTHER INFORMATION: Hv-CDR3

<400> SEQUENCE: 22

Arg Arg Arg Gly Val Pro Arg Arg Asp Asp Phe Asp Ile
1               5                   10

<210> SEQ ID NO 23
<211> LENGTH: 13
<212> TYPE: PRT
<213> ORGANISM: Artificial sequence
<220> FEATURE:
<223> OTHER INFORMATION: Hv-CDR3

<400> SEQUENCE: 23

Arg Arg Ile Gly Val Pro Arg Arg Asp Ala Phe Asp Ile
1               5                   10

<210> SEQ ID NO 24
<211> LENGTH: 13
<212> TYPE: PRT
<213> ORGANISM: Artificial sequence
<220> FEATURE:
<223> OTHER INFORMATION: Hv-CDR3

<400> SEQUENCE: 24

Arg Arg Ile Gly Val Pro Arg Arg Asp Ser Phe Asp Ile
1               5                   10

<210> SEQ ID NO 25
<211> LENGTH: 13
<212> TYPE: PRT
<213> ORGANISM: Artificial sequence
<220> FEATURE:
<223> OTHER INFORMATION: Hv-CDR3

<400> SEQUENCE: 25

Arg Arg Ile Gly Val Pro Arg Arg Asp Ser Phe Asp Met
1               5                   10

<210> SEQ ID NO 26
<211> LENGTH: 13
<212> TYPE: PRT
<213> ORGANISM: Artificial sequence
<220> FEATURE:
<223> OTHER INFORMATION: Hv-CDR3

<400> SEQUENCE: 26

Arg Arg Ile Gly Val Pro Arg Arg Asp Asp Phe Asp Ile
1               5                   10

<210> SEQ ID NO 27
<211> LENGTH: 13
<212> TYPE: PRT
<213> ORGANISM: Artificial sequence
<220> FEATURE:
<223> OTHER INFORMATION: Hv-CDR3

<400> SEQUENCE: 27

Arg Arg Ile Gly Val Pro Arg Arg Asp Glu Phe Asp Ile

```
<210> SEQ ID NO 28
<211> LENGTH: 13
<212> TYPE: PRT
<213> ORGANISM: Artificial sequence
<220> FEATURE:
<223> OTHER INFORMATION: Hv-CDR3

<400> SEQUENCE: 28

Arg Arg Ile Gly Ile Pro Arg Arg Asp Ala Phe Asp Ile
1               5                   10

<210> SEQ ID NO 29
<211> LENGTH: 13
<212> TYPE: PRT
<213> ORGANISM: Artificial sequence
<220> FEATURE:
<223> OTHER INFORMATION: Hv-CDR3

<400> SEQUENCE: 29

Arg Arg Ile Gly Ile Pro Arg Arg Asp Glu Phe Asp Ile
1               5                   10

<210> SEQ ID NO 30
<211> LENGTH: 13
<212> TYPE: PRT
<213> ORGANISM: Artificial sequence
<220> FEATURE:
<223> OTHER INFORMATION: Hv-CDR3

<400> SEQUENCE: 30

Arg Arg Thr Gly Ala Pro Arg Arg Asp Ala Phe Asp Ile
1               5                   10

<210> SEQ ID NO 31
<211> LENGTH: 13
<212> TYPE: PRT
<213> ORGANISM: Artificial sequence
<220> FEATURE:
<223> OTHER INFORMATION: Hv-CDR3

<400> SEQUENCE: 31

Arg Arg Thr Gly Ser Pro Arg Arg Asp Ala Phe Asp Ile
1               5                   10

<210> SEQ ID NO 32
<211> LENGTH: 13
<212> TYPE: PRT
<213> ORGANISM: Artificial sequence
<220> FEATURE:
<223> OTHER INFORMATION: Hv-CDR3

<400> SEQUENCE: 32

Arg Arg Thr Gly Leu Pro Arg Arg Asp Ala Phe Asp Ile
1               5                   10

<210> SEQ ID NO 33
<211> LENGTH: 13
<212> TYPE: PRT
<213> ORGANISM: Artificial sequence
<220> FEATURE:
<223> OTHER INFORMATION: Hv-CDR3

<400> SEQUENCE: 33

Arg Arg Thr Gly Ile Pro Arg Arg Asp Glu Phe Asp Ile
1               5                   10
```

<210> SEQ ID NO 34
<211> LENGTH: 106
<212> TYPE: PRT
<213> ORGANISM: Artificial sequence
<220> FEATURE:
<223> OTHER INFORMATION: 559A-M0162-A04 light chain

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys
            100                 105

<210> SEQ ID NO 35
<211> LENGTH: 102
<212> TYPE: PRT
<213> ORGANISM: Artificial sequence
<220> FEATURE:
<223> OTHER INFORMATION: 559A-M0162-A04 light chain and germline light
      chain comparison

<400> SEQUENCE: 35

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Leu Leu Ile Tyr
        35                  40                  45

Ala Ser Leu Glu Ser Gly Val Pro Ser Arg Phe Ser Gly Ser Gly Ser
    50                  55                  60

Gly Thr Glu Phe Thr Leu Thr Ile Ser Ser Leu Gln Pro Asp Asp Phe
65                  70                  75                  80

Ala Thr Tyr Tyr Cys Gln Gln Tyr Asn Tyr Trp Thr Phe Gly Gln Gly
                85                  90                  95

Thr Lys Val Glu Ile Lys
            100

<210> SEQ ID NO 36
<211> LENGTH: 106
<212> TYPE: PRT
<213> ORGANISM: Artificial sequence
<220> FEATURE:
<223> OTHER INFORMATION: Germline light chain

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 37
<211> LENGTH: 122
<212> TYPE: PRT
<213> ORGANISM: Artificial sequence
<220> FEATURE:
<223> OTHER INFORMATION: 559A-M0162-A04 heavy chain

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ile Met Met Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Thr Gly Ile Pro Arg Arg Asp Ala Phe Asp Ile Trp
            100                 105                 110

Gly Gln Gly Thr Met Val Thr Val Ser Ser
        115                 120

<210> SEQ ID NO 38
<211> LENGTH: 104
<212> TYPE: PRT
<213> ORGANISM: Artificial sequence
<220> FEATURE:
<223> OTHER INFORMATION: 559A-M0162-A04 heavy chain and germline
      comparison

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Met
            20                  25                  30

Trp Val Arg Gln Ala Pro Gly Lys Gly Leu Glu Trp Val Ser Ile Ser
        35                  40                  45

Gly Gly Thr Tyr Ala Asp Ser Val Lys Gly Arg Phe Thr Ile Ser Arg
    50                  55                  60

Asp Asn Ser Lys Asn Thr Leu Tyr Leu Gln Met Asn Ser Leu Arg Ala
65                  70                  75                  80

Glu Asp Thr Ala Val Tyr Tyr Cys Ala Ala Phe Asp Ile Trp Gly Gln
                85                  90                  95

```
Gly Thr Met Val Thr Val Ser Ser
            100

<210> SEQ ID NO 39
<211> LENGTH: 113
<212> TYPE: PRT
<213> ORGANISM: Artificial sequence
<220> FEATURE:
<223> OTHER INFORMATION: Germline heavy chain

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Phe Asp Ile Trp Gly Gln Gly Thr Met Val Thr Val Ser
            100                 105                 110

Ser

<210> SEQ ID NO 40
<211> LENGTH: 248
<212> TYPE: PRT
<213> ORGANISM: H. sapiens

<400> SEQUENCE: 40

Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
        35                  40                  45

Leu Pro Leu Gln Asp Val Trp Arg Ile Tyr Ser Gly Ile Leu Asn Leu
    50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Ser Leu Pro Ser Lys Gly Asp Thr Ser Thr Ile Tyr Thr Asn Cys Trp
            115                 120                 125

Val Thr Gly Trp Gly Phe Ser Lys Glu Lys Gly Glu Ile Gln Asn Ile
        130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Asp Ala Cys Lys Gly Asp Ser Gly Gly Pro Leu
            180                 185                 190
```

```
Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
                245
```

<210> SEQ ID NO 41
<211> LENGTH: 248
<212> TYPE: PRT
<213> ORGANISM: Artificial sequence
<220> FEATURE:
<223> OTHER INFORMATION: (klkb1)-Mut1-forPichia

<400> SEQUENCE: 41

```
Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
        35                  40                  45

Leu Pro Leu Gln Asp Val Trp Arg Ile Tyr Ser Gly Ile Leu Asn Leu
    50                  55                  60

Ser Asp Ile Thr Lys Asp Thr Pro Phe Ser Gln Ile Lys Glu Ile Ile
65                  70                  75                  80

Ile His Gln Asn Tyr Lys Val Ala Glu Gly Ala His Asp Ile Ala Leu
                85                  90                  95

Ile Lys Leu Gln Ala Pro Leu Asn Tyr Thr Glu Phe Gln Lys Pro Ile
            100                 105                 110

Ser Leu Pro Ala Ala Gly Asp Thr Ser Thr Ile Tyr Thr Asn Cys Trp
        115                 120                 125

Val Thr Gly Trp Gly Phe Ser Lys Glu Lys Gly Glu Ile Gln Asn Ile
    130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Asp Ala Cys Lys Gly Asp Ser Gly Gly Pro Leu
            180                 185                 190

Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
    210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
                245
```

<210> SEQ ID NO 42
<211> LENGTH: 248
<212> TYPE: PRT
<213> ORGANISM: Artificial sequence
<220> FEATURE:
<223> OTHER INFORMATION: (klkb1)-Mut2-forPichia

```
<400> SEQUENCE: 42

Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
        35                  40                  45

Leu Pro Leu Gln Asp Val Trp Arg Ile Tyr Ser Gly Ile Leu Asn Leu
    50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Ser Leu Pro Ser Lys Gly Asp Thr Ser Thr Ile Tyr Thr Asn Cys Trp
        115                 120                 125

Val Thr Gly Trp Gly Phe Ser Lys Glu Lys Gly Glu Ile Gln Asn Ile
    130                 135                 140

Leu Gln Lys Val Asn Ile Pro Leu Val Thr Asn Glu Glu Cys Gln Lys
145                 150                 155                 160

Ala Tyr Ala Asp Ala Lys Ile Ala Gln Ala Met Val Cys Ala Gly Tyr
                165                 170                 175

Lys Glu Gly Gly Lys Asp Ala Cys Lys Gly Asp Ser Gly Gly Pro Leu
            180                 185                 190

Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
    210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
                245

<210> SEQ ID NO 43
<211> LENGTH: 248
<212> TYPE: PRT
<213> ORGANISM: Artificial sequence
<220> FEATURE:
<223> OTHER INFORMATION: (klkb1)-Mut3-forPichia

<400> SEQUENCE: 43

Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
        35                  40                  45

Leu Pro Leu Gln Asp Val Trp Arg Ile Tyr Ser Gly Ile Leu Asn Leu
    50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
```

```
            100                 105                 110
Ser Leu Pro Ser Lys Gly Asp Thr Ser Thr Ile Tyr Thr Asn Cys Trp
        115                 120                 125

Val Thr Gly Trp Gly Phe Ser Lys Glu Lys Gly Glu Ile Gln Asn Ile
    130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Ala Ala Cys Ala Gly Ala Ser Gly Gly Pro Leu
            180                 185                 190

Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
    210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
                245

<210> SEQ ID NO 44
<211> LENGTH: 248
<212> TYPE: PRT
<213> ORGANISM: Artificial sequence
<220> FEATURE:
<223> OTHER INFORMATION: (klkb1)-Mut4-forPichia

<400> SEQUENCE: 44

Ile Val Gly Gly Thr Ala Ser Ala Ala Gly Glu Trp Pro Trp Gln Val
1               5                   10                  15

Ser Leu Gln Val Lys Leu Thr Ala Gln Arg His Leu Cys Gly Gly Ser
                20                  25                  30

Leu Ile Gly His Gln Trp Val Leu Thr Ala Ala His Cys Phe Asp Gly
            35                  40                  45

Leu Pro Leu Gln Asp Val Trp Arg Ile Tyr Ser Gly Ile Leu Asn Leu
        50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Ser Leu Pro Ser Lys Gly Asp Thr Ser Thr Ile Tyr Thr Asn Cys Trp
        115                 120                 125

Val Thr Gly Trp Gly Phe Ser Lys Glu Lys Gly Glu Ile Gln Asn Ile
    130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Asp Ala Cys Lys Gly Asp Ser Gly Gly Pro Leu
            180                 185                 190

Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
    210                 215                 220
```

-continued

```
                210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
                245

<210> SEQ ID NO 45
<211> LENGTH: 248
<212> TYPE: PRT
<213> ORGANISM: Artificial sequence
<220> FEATURE:
<223> OTHER INFORMATION: (klkb1)-parentforPichia

<400> SEQUENCE: 45

Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
                20                  25                  30

Leu Ile Gly His Gln Trp Val Leu Thr Ala Ala His Cys Phe Asp Gly
            35                  40                  45

Leu Pro Leu Gln Asp Val Trp Arg Ile Tyr Ser Gly Ile Leu Asn Leu
        50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Ser Leu Pro Ser Lys Gly Asp Thr Ser Thr Ile Tyr Thr Asn Cys Trp
        115                 120                 125

Val Thr Gly Trp Gly Phe Ser Lys Glu Lys Gly Glu Ile Gln Asn Ile
130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Asp Ala Cys Lys Gly Asp Ser Gly Gly Pro Leu
            180                 185                 190

Val Cys Lys His Asn Gly Met Trp Arg Leu Val Gly Ile Thr Ser Trp
        195                 200                 205

Gly Glu Gly Cys Ala Arg Arg Glu Gln Pro Gly Val Tyr Thr Lys Val
    210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
                245

<210> SEQ ID NO 46
<211> LENGTH: 451
<212> TYPE: PRT
<213> ORGANISM: Artificial sequence
<220> FEATURE:
<223> OTHER INFORMATION: DX-2930 Heavy Chain

<400> SEQUENCE: 46

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser His Tyr
         20                  25                  30

Ile Met Met Trp Val Arg Gln Ala Pro Gly Lys Gly Leu Glu Trp Val
             35                  40                  45

Ser Gly Ile Tyr Ser Ser Gly Gly Ile Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Tyr Arg Arg Ile Gly Val Pro Arg Arg Asp Glu Phe Asp Ile Trp
             100                 105                 110

Gly Gln Gly Thr Met Val Thr Val Ser Ser Ala Ser Thr Lys Gly Pro
         115                 120                 125

Ser Val Phe Pro Leu Ala Pro Ser Ser Lys Ser Thr Ser Gly Gly Thr
     130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
```

```
                 435              440             445
Ser Pro Gly
    450

<210> SEQ ID NO 47
<211> LENGTH: 213
<212> TYPE: PRT
<213> ORGANISM: Artificial sequence
<220> FEATURE:
<223> OTHER INFORMATION: Amino acids from Pkal

<400> SEQUENCE: 47

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 48
<211> LENGTH: 4
<212> TYPE: PRT
<213> ORGANISM: Artificial sequence
<220> FEATURE:
<223> OTHER INFORMATION: Amino acids from Pkal

<400> SEQUENCE: 48

Ser Trp Gly Glu
1

<210> SEQ ID NO 49
<211> LENGTH: 5
<212> TYPE: PRT
<213> ORGANISM: Artificial sequence
<220> FEATURE:
<223> OTHER INFORMATION: Amino acids from Pkal

<400> SEQUENCE: 49
```

```
Asp Ala Cys Lys Gly
1               5

<210> SEQ ID NO 50
<211> LENGTH: 6
<212> TYPE: PRT
<213> ORGANISM: Artificial sequence
<220> FEATURE:
<223> OTHER INFORMATION: Amino acids from Pkal

<400> SEQUENCE: 50

Thr Ser Trp Gly Glu Gly
1               5

<210> SEQ ID NO 51
<211> LENGTH: 19
<212> TYPE: PRT
<213> ORGANISM: Artificial sequence
<220> FEATURE:
<223> OTHER INFORMATION: Amino acids from Pkal

<400> SEQUENCE: 51

Leu Val Thr Asn Glu Glu Cys Gln Lys Arg Tyr Gln Asp Tyr Lys Ile
1               5                   10                  15

Thr Gln Gln

<210> SEQ ID NO 52
<211> LENGTH: 14
<212> TYPE: PRT
<213> ORGANISM: Artificial sequence
<220> FEATURE:
<223> OTHER INFORMATION: Amino acids from Pkal

<400> SEQUENCE: 52

Trp Val Thr Gly Trp Gly Phe Ser Lys Glu Lys Gly Glu Ile
1               5                   10

<210> SEQ ID NO 53
<211> LENGTH: 10
<212> TYPE: PRT
<213> ORGANISM: Artificial sequence
<220> FEATURE:
<223> OTHER INFORMATION: Amino acids from Pkal

<400> SEQUENCE: 53

Ala Cys Lys Gly Asp Ser Gly Gly Pro Leu
1               5                   10

<210> SEQ ID NO 54
<211> LENGTH: 5
<212> TYPE: PRT
<213> ORGANISM: Artificial sequence
<220> FEATURE:
<223> OTHER INFORMATION: Amino acids from Pkal

<400> SEQUENCE: 54

Ser Trp Gly Asp Ile
1               5

<210> SEQ ID NO 55
<211> LENGTH: 8
<212> TYPE: PRT
<213> ORGANISM: Artificial sequence
<220> FEATURE:
<223> OTHER INFORMATION: Amino acids from Pkal
```

```
<400> SEQUENCE: 55

His Asp Ile Ala Leu Ile Lys Leu
1               5

<210> SEQ ID NO 56
<211> LENGTH: 15
<212> TYPE: PRT
<213> ORGANISM: Artificial sequence
<220> FEATURE:
<223> OTHER INFORMATION: Amino acids from Pkal

<400> SEQUENCE: 56

Thr Pro Phe Ser Gln Ile Lys Glu Ile Ile His Gln Asn Tyr
1               5                   10                  15

<210> SEQ ID NO 57
<211> LENGTH: 16
<212> TYPE: PRT
<213> ORGANISM: Artificial sequence
<220> FEATURE:
<223> OTHER INFORMATION: Amino acids from Pkal

<400> SEQUENCE: 57

Ala His Cys Phe Asp Gly Leu Pro Leu Gln Asp Val Trp Arg Ile Tyr
1               5                   10                  15

<210> SEQ ID NO 58
<211> LENGTH: 13
<212> TYPE: PRT
<213> ORGANISM: Artificial sequence
<220> FEATURE:
<223> OTHER INFORMATION: Hv-CDR3
<220> FEATURE:
<221> NAME/KEY: MISC_FEATURE
<222> LOCATION: (1)..(1)
<223> OTHER INFORMATION: Arg or Gln
<220> FEATURE:
<221> NAME/KEY: MISC_FEATURE
<222> LOCATION: (3)..(3)
<223> OTHER INFORMATION: Thr, Ile, Arg, Ser or Pro
<220> FEATURE:
<221> NAME/KEY: MISC_FEATURE
<222> LOCATION: (5)..(5)
<223> OTHER INFORMATION: Val, Ile or Leu
<220> FEATURE:
<221> NAME/KEY: MISC_FEATURE
<222> LOCATION: (8)..(8)
<223> OTHER INFORMATION: Arg or Trp
<220> FEATURE:
<221> NAME/KEY: MISC_FEATURE
<222> LOCATION: (9)..(9)
<223> OTHER INFORMATION: Asp or Asn
<220> FEATURE:
<221> NAME/KEY: MISC_FEATURE
<222> LOCATION: (10)..(10)
<223> OTHER INFORMATION: Ala, Ser, Asp, Glu or Val
<220> FEATURE:
<221> NAME/KEY: MISC_FEATURE
<222> LOCATION: (11)..(11)
<223> OTHER INFORMATION: Phe or Leu
<220> FEATURE:
<221> NAME/KEY: MISC_FEATURE
<222> LOCATION: (12)..(12)
<223> OTHER INFORMATION: Asp, Glu or Asn
<220> FEATURE:
<221> NAME/KEY: MISC_FEATURE
<222> LOCATION: (13)..(13)
<223> OTHER INFORMATION: Ile, Asn, Met or Ser

<400> SEQUENCE: 58

Xaa Arg Xaa Gly Xaa Pro Arg Xaa Xaa Xaa Xaa Xaa Xaa
1               5                   10
```

<210> SEQ ID NO 59
<211> LENGTH: 11
<212> TYPE: PRT
<213> ORGANISM: Artificial sequence
<220> FEATURE:
<223> OTHER INFORMATION: Synthetic

<400> SEQUENCE: 59

Arg Ala Ser Gln Ser Ile Ser Ser Trp Leu Ala
1               5                   10

<210> SEQ ID NO 60
<211> LENGTH: 7
<212> TYPE: PRT
<213> ORGANISM: Artificial sequence
<220> FEATURE:
<223> OTHER INFORMATION: Synthetic

<400> SEQUENCE: 60

Lys Ala Ser Thr Leu Glu Ser
1               5

<210> SEQ ID NO 61
<211> LENGTH: 8
<212> TYPE: PRT
<213> ORGANISM: Artificial sequence
<220> FEATURE:
<223> OTHER INFORMATION: Synthetic

<400> SEQUENCE: 61

Gln Gln Tyr Asn Thr Tyr Trp Thr
1               5

<210> SEQ ID NO 62
<211> LENGTH: 5
<212> TYPE: PRT
<213> ORGANISM: Artificial sequence
<220> FEATURE:
<223> OTHER INFORMATION: Synthetic

<400> SEQUENCE: 62

His Tyr Ile Met Met
1               5

<210> SEQ ID NO 63
<211> LENGTH: 17
<212> TYPE: PRT
<213> ORGANISM: Artificial sequence
<220> FEATURE:
<223> OTHER INFORMATION: Synthetic

<400> SEQUENCE: 63

Gly Ile Tyr Ser Ser Gly Gly Ile Thr Val Tyr Ala Asp Ser Val Lys
1               5                   10                  15

Gly

```
<210> SEQ ID NO 64
<211> LENGTH: 13
<212> TYPE: PRT
<213> ORGANISM: Artificial sequence
<220> FEATURE:
<223> OTHER INFORMATION: Synthetic

<400> SEQUENCE: 64

Arg Arg Thr Gly Ile Pro Arg Arg Asp Ala Phe Asp Ile
1               5                   10
```

UNITED STATES PATENT AND TRADEMARK OFFICE
CERTIFICATE OF CORRECTION

PATENT NO.         : 12,110,343 B2
APPLICATION NO.    : 17/684460
DATED              : October 8, 2024
INVENTOR(S)        : Nixon et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 370 days.

Signed and Sealed this
Thirteenth Day of May, 2025

Coke Morgan Stewart
*Acting Director of the United States Patent and Trademark Office*